United States Patent
Sander et al.

(10) Patent No.: US 8,577,619 B2
(45) Date of Patent: Nov. 5, 2013

(54) MODELS FOR COMBINATORIAL PERTURBATIONS OF LIVING BIOLOGICAL SYSTEMS

(75) Inventors: Chris Sander, Cambridge, MA (US); Sven Nelander, Gothenburg (SE); Wei Qing Wang, Jersey City, NJ (US); Peter Gennemark, Kungsbacka (SE); Björn Nilsson, Lund (SE)

(73) Assignee: Sloan Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 12/994,723

(22) PCT Filed: May 27, 2009

(86) PCT No.: PCT/US2009/045353
§ 371 (c)(1),
(2), (4) Date: Jun. 8, 2011

(87) PCT Pub. No.: WO2009/155009
PCT Pub. Date: Dec. 23, 2009

(65) Prior Publication Data
US 2011/0264420 A1     Oct. 27, 2011

Related U.S. Application Data

(60) Provisional application No. 61/056,331, filed on May 27, 2008, provisional application No. 61/103,540, filed on Oct. 7, 2008.

(51) Int. Cl.
*G06F 19/12* (2011.01)
*G06F 19/00* (2011.01)

(52) U.S. Cl.
USPC ......................................................... 702/19

(58) Field of Classification Search
None
See application file for complete search history.

(56) References Cited

U.S. PATENT DOCUMENTS

| | | | |
|---|---|---|---|
| 6,132,969 A | 10/2000 | Stoughton et al. | |
| 2004/0088116 A1 | 5/2004 | Khalil et al. | |
| 2005/0143628 A1 | 6/2005 | Dai | |
| 2005/0171746 A1 | 8/2005 | Thalhammer-Reyero | |
| 2006/0235670 A1 | 10/2006 | Vujasinovic | |
| 2007/0016390 A1 | 1/2007 | Bernardo et al. | |
| 2007/0226157 A1 | 9/2007 | Kam | |
| 2008/0009545 A1 | 1/2008 | Chen | |
| 2008/0027695 A1 | 1/2008 | Balgi | |

FOREIGN PATENT DOCUMENTS

WO    2009155009 A1    12/2009

OTHER PUBLICATIONS

Zupan et al. (Bioinformatics (2003) vol. 19, No. 3, pp. 383-389).*
Nelander et al., "Beyond Epistasis Analysis: Combinatorial Perturbation Analysis by Dynamic Modeling", "Abstract of oral presentation at PLoS Track at ISMB/ECCB 2007", Jun. 2, 2007, from Internet URL www.iscb.org/uploaded/css/nelander_20070602185117.pdf, Publisher: ISMB/ECCB.
Hill et al., "Systems and Methods fpr Modeling and Analyzing Networks", May 22, 2008, Published in: WIPO, WO2008/060620.
Turkeli, "Supplemental European Search Report, EP09767321," European Patent Office, The Hauge, May 9, 2011.
Ribba, B., et al., "A Multiscale mathematical model of cancer, and its use in analyzing irradation therapies," Theoretical Biology and Medical Modelling 2006,3:7, Feb. 10, 2006 [retrieved Aug. 19, 2009] Retrieved from the Internet. <URL: http://www.tbiomed.com/contentlpdf/1742-4682-3-7.pdf>, pp. 1-19 Entire document, especially: Abstract; p. 1, col. 2, para '1; p. 2, col. 2, para 1; p. 3, col. 2, para 2; p. 5, Fig. 3; p. 7, col. 1, para 2 thru col. 2, para 4, Eqn. 8 and Table 4; p. 13, col. 1 para 2 thru col. 2, para 1; p. 17, col. 1, para 2; p. 18, col. 1.

* cited by examiner

*Primary Examiner* — Lori A Clow
(74) *Attorney, Agent, or Firm* — Evans & Molinelli PLLC; Eugene J. Molinelli

(57) ABSTRACT

Techniques for modeling living biological systems include receiving constant values for multiple interaction factors $w_{ij}$. A set of initial state values is received for state variables that indicate relevant properties of a living biological system. Also received is a set of trial values for perturbation variables that indicate factors that might affect one or more of the relevant properties of the biological system. A temporal change in a value for a particular state variable is determined based on a non-linear transformation of a sum of the trial value for the perturbation that affects the particular state added to a sum of all non-zero values for a product of $w_{ij}$ and a state variable over all state variables.
In some embodiments, measurement-based values are received for a measurable subset of the state variables. Values for the constant interaction factors $w_{ij}$ are determined based on the measurement-based values.

34 Claims, 16 Drawing Sheets

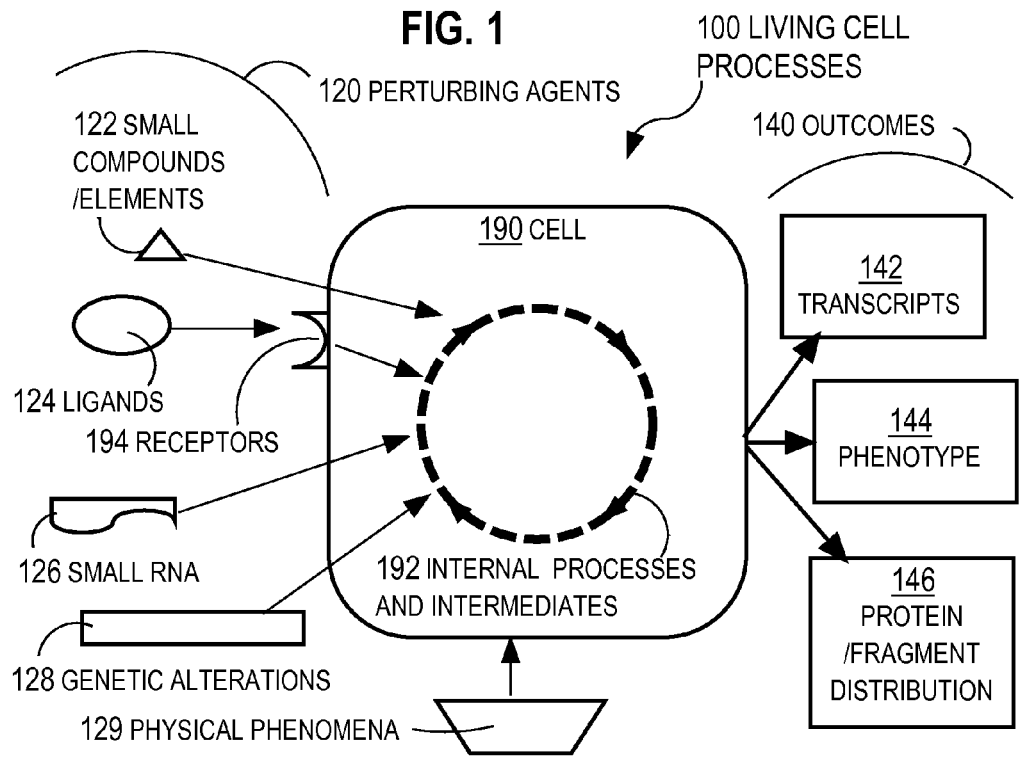
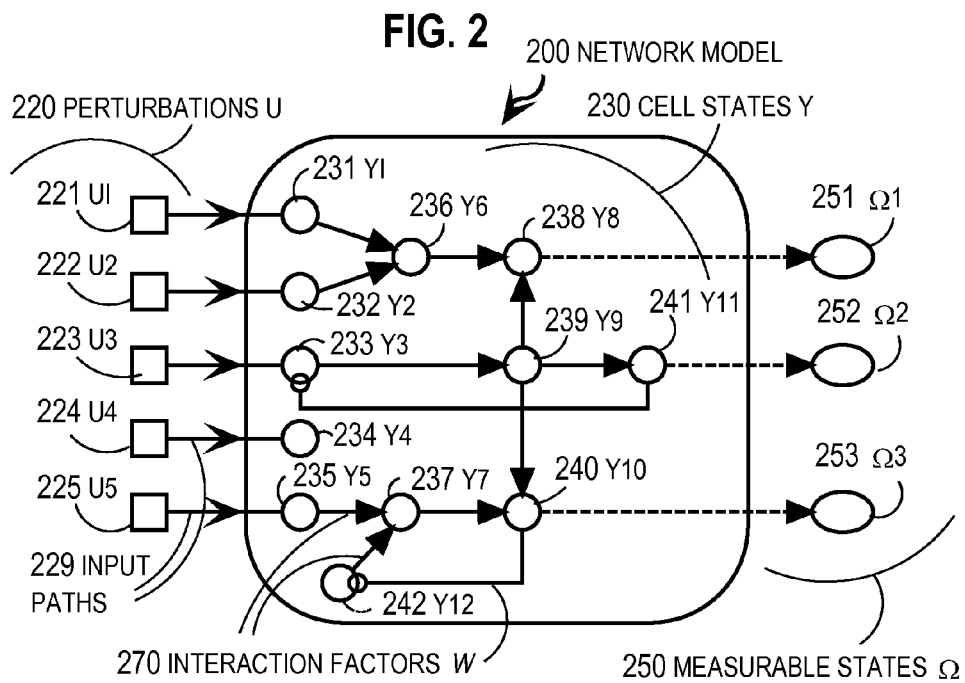

FIG. 3

300 STRUCTURE MATRIX S FOR INTERACTION FACTORS

304 ROW NUMBER I (DESTINATION STATE)

302 COLUMN NUMBER J (SOURCE STATE)

|    | 1 | 2 | 3 | 4 | 5 | 6 | 7 | 8 | 9 | 10 | 11 | 12 |
|----|---|---|---|---|---|---|---|---|---|----|----|----|
| 1  | 0 | 0 | 0 | 0 | 0 | 0 | 0 | 0 | 0 | 0  | 0  | 0  |
| 2  | 0 | 0 | 0 | 0 | 0 | 0 | 0 | 0 | 0 | 0  | 0  | 0  |
| 3  | 0 | 0 | 0 | 0 | 0 | 0 | 0 | 0 | 0 | 0  | 1  | 0  |
| 4  | 0 | 0 | 0 | 0 | 0 | 0 | 0 | 0 | 0 | 0  | 0  | 0  |
| 5  | 0 | 0 | 0 | 0 | 0 | 0 | 0 | 0 | 0 | 0  | 0  | 0  |
| 6  | 1 | 1 | 0 | 0 | 0 | 0 | 0 | 0 | 0 | 0  | 0  | 0  |
| 7  | 0 | 0 | 0 | 0 | 1 | 0 | 0 | 0 | 0 | 0  | 0  | 1  |
| 8  | 0 | 0 | 0 | 0 | 0 | 1 | 0 | 0 | 1 | 0  | 0  | 0  |
| 9  | 0 | 0 | 1 | 0 | 0 | 0 | 0 | 0 | 0 | 0  | 0  | 0  |
| 10 | 0 | 0 | 0 | 0 | 0 | 0 | 1 | 0 | 1 | 0  | 0  | 0  |
| 11 | 0 | 0 | 0 | 0 | 0 | 0 | 0 | 0 | 1 | 0  | 0  | 0  |
| 12 | 0 | 0 | 0 | 0 | 0 | 0 | 0 | 0 | 0 | 1  | 0  | 0  |

310 STRUCTURE MATRIX ELEMENT $S_{12,6}$

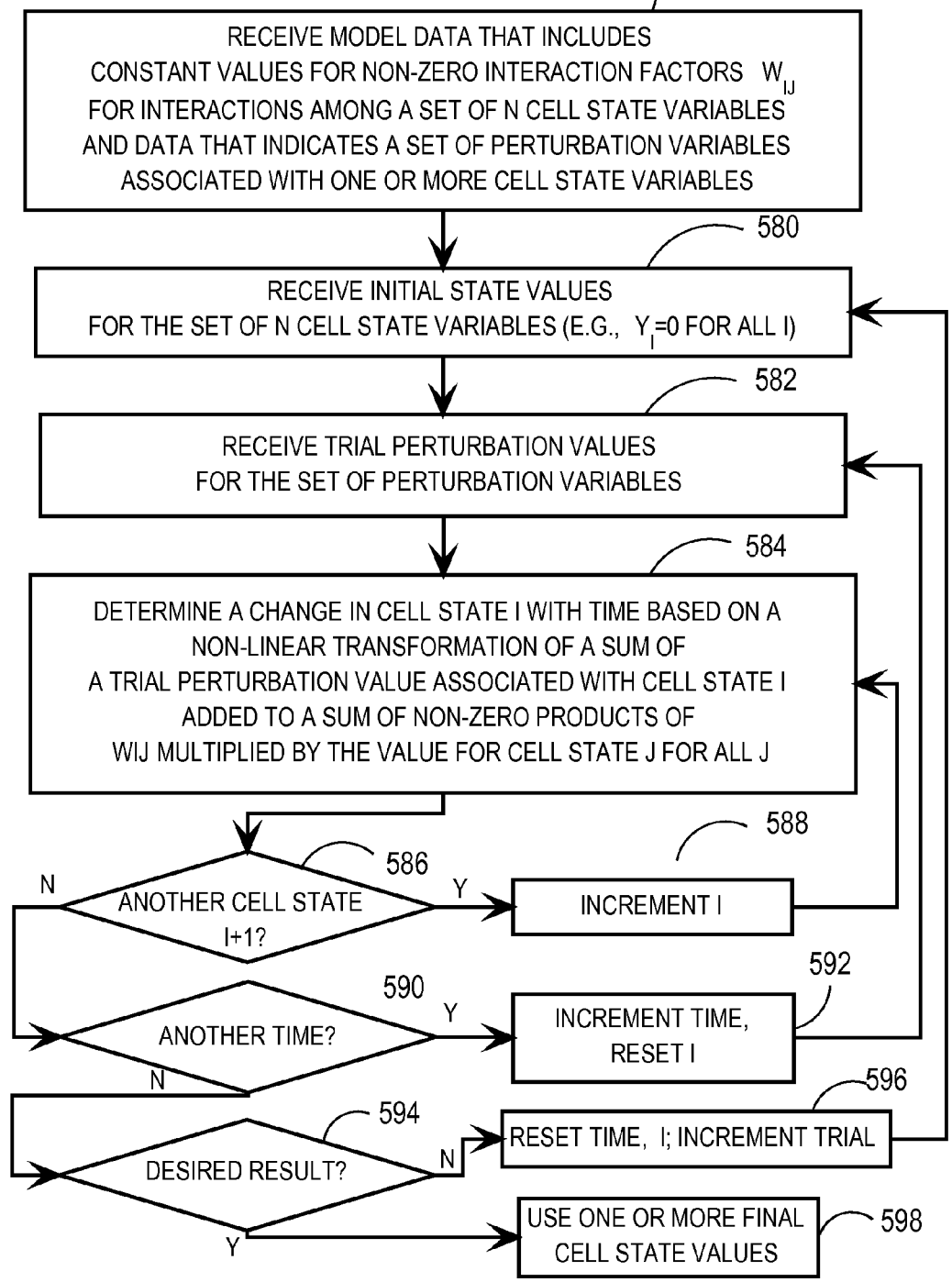

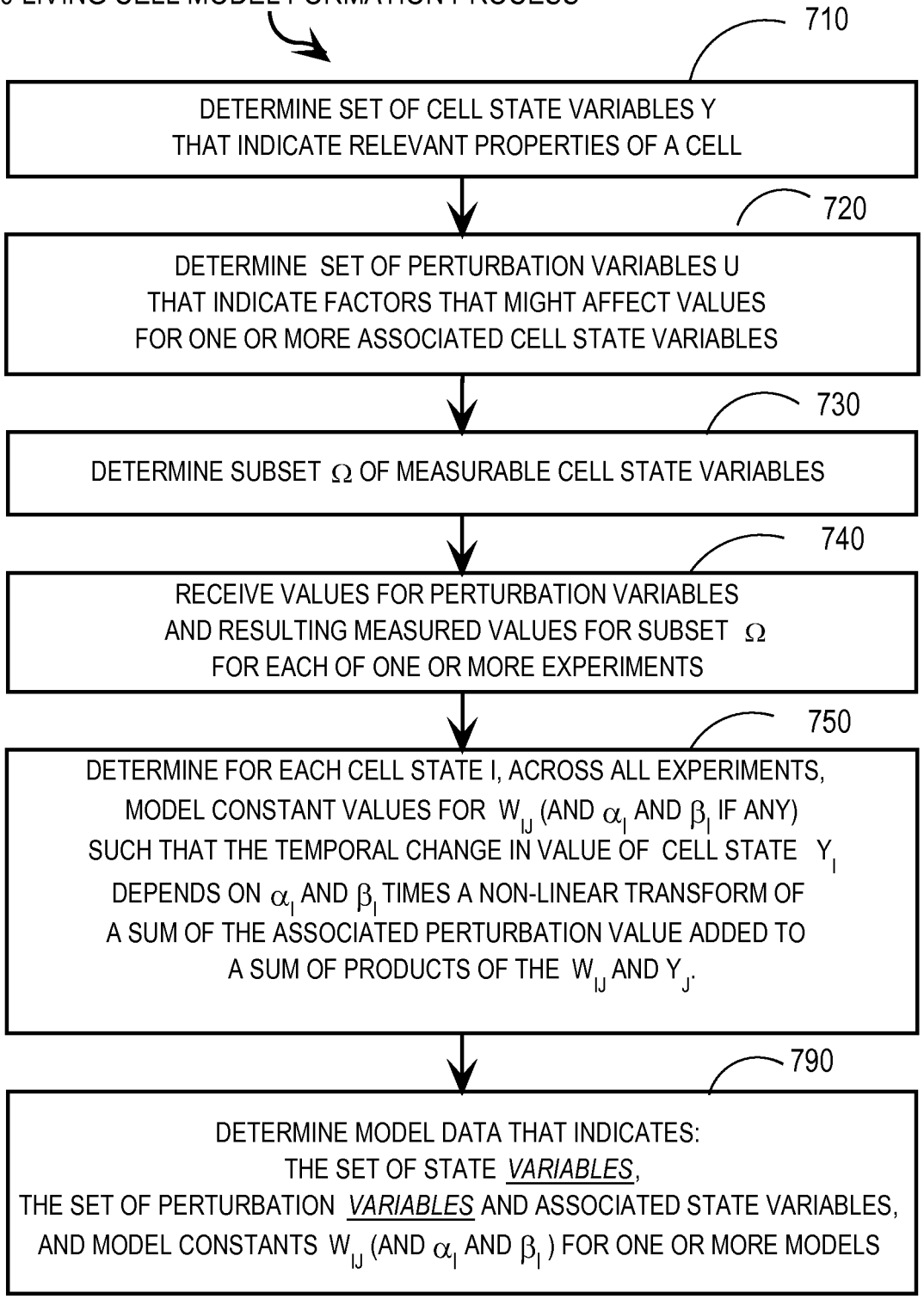

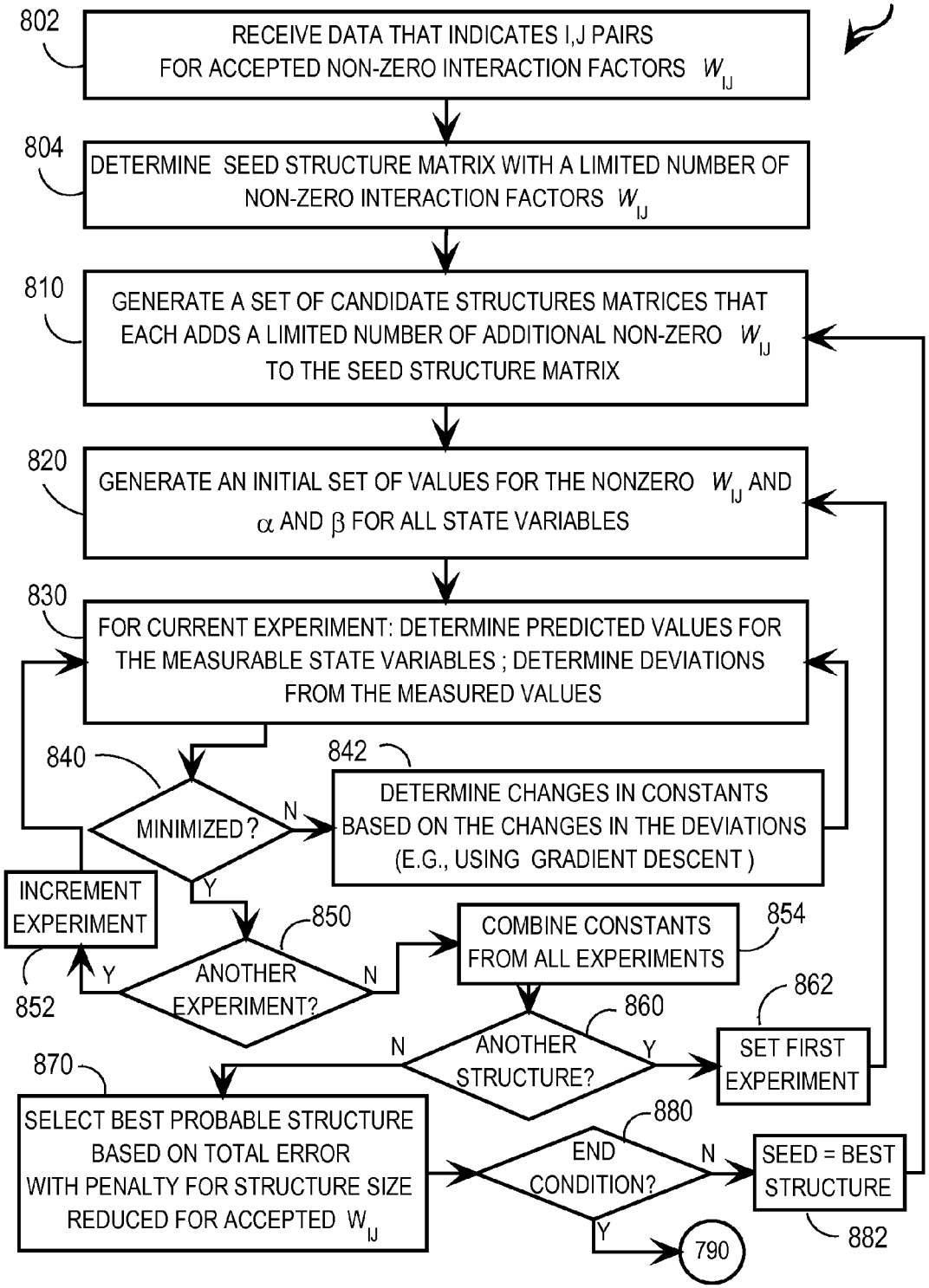

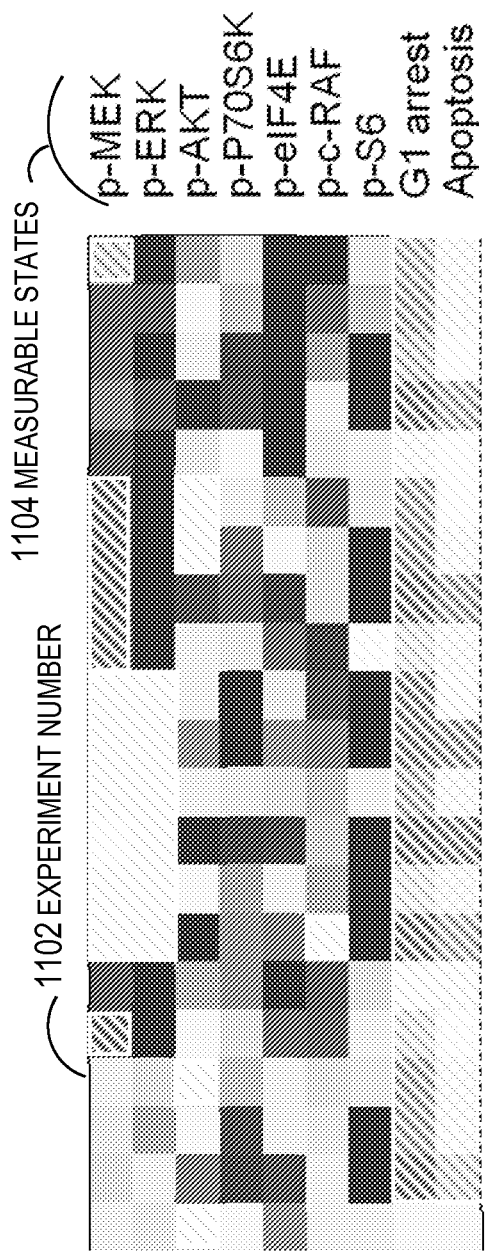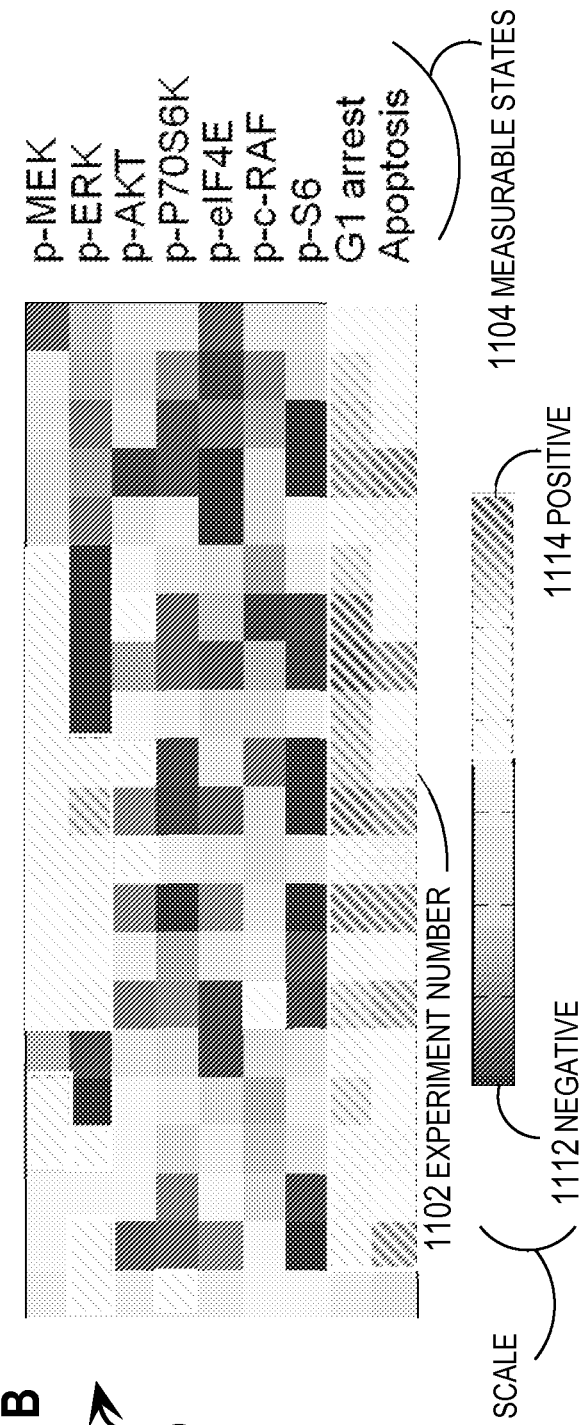
FIG. 11A 1100 OBSERVED VALUES
FIG. 11B 1150 PREDICTED VALUES

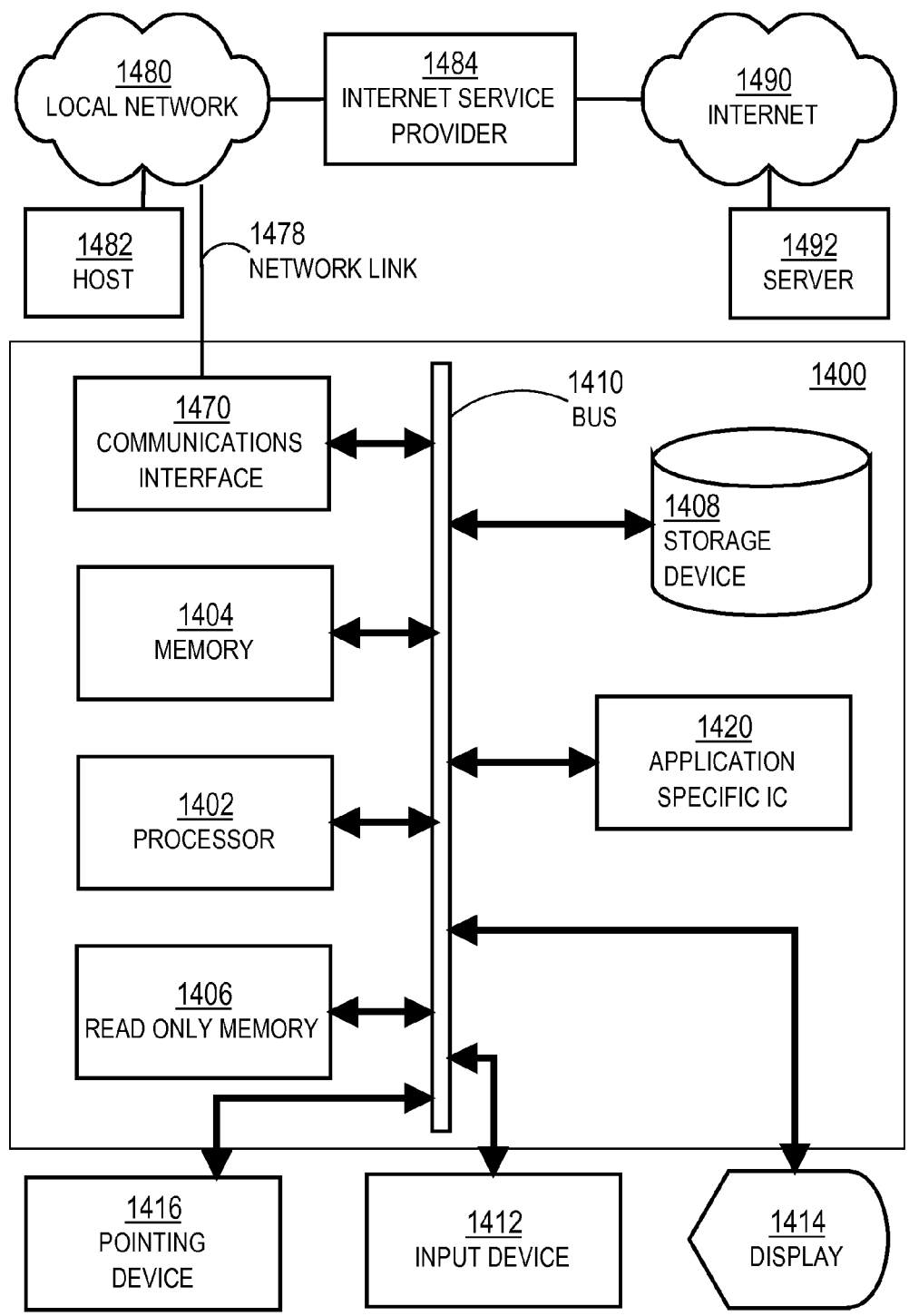

MODELS FOR COMBINATORIAL PERTURBATIONS OF LIVING BIOLOGICAL SYSTEMS

CROSS-REFERENCE TO RELATED APPLICATIONS

This present application is a national stage application of PCT Application No. PCT/US2009/045353 filed on May 27, 2009 and claims priority of U.S. Provisional Appln. 61/056,331, filed May 27, 2008, the entire contents of which are hereby incorporated by reference as if fully set forth herein, under 35 U.S.C. §119(e). This application also claims benefit of Provisional Appln. 61/103,540, filed Oct. 7, 2008, under 35 U.S.C. §119(e).

BACKGROUND OF THE INVENTION

1. Field of the Invention

The present invention relates to modeling signaling pathways in biological systems based on observations of consequences of perturbations, such as drug treatments or genetic alterations.

2. Description of the Related Art

In molecular biology, a targeted perturbation typically inhibits or activates the function of bio-molecules, e.g., as a result of drug action, small RNA interference, or genetic or epigenetic change. In a single experiment, targeted perturbations can be applied either singly or in combination. Combined perturbation by several agents can be much more informative than that by a single agent, as its effects typically reveal downstream genetic interactions (called epistasis) within the system, such as non-additive synergistic or antagonistic interactions. In addition, a large number of independently informative experiments can be performed if in each experiment a different small set of, e.g., two or three, perturbing agents (perturbants) is chosen from a larger arsenal. Thus, combinatorial perturbations are potentially powerful investigational tools for extracting information about pathways of molecular interactions in cells (such as A inactivates B, or X and Y are in the same pathway). (See, for example, Avery and Wasserman, "Ordering gene function: the interpretation of epistasis in regulatory hierarchies," Trends Genet vol. 8, pp 312-316, 1992; Kelley and Ideker, "Systematic interpretation of genetic interactions using protein networks," Nat Biotechnol, vol. 23, pp 561-566, 2005; Segre D, Deluna A, Church G M, Kishony R "Modular epistasis in yeast metabolism," Nat Genet vol. 37, pp 77-83, 2005; Yeh P, Tschumi A I, Kishony R, "Functional classification of drugs by properties of their pairwise interactions," Nat Genet vol. 38, pp 489-494, 2006; Lehár J, Zimmermann G R, Krueger A S, Molnar R A, Ledell J T, Heilbut A M, Short G F, Giusti L C, Nolan G P, Magid O A, Lee M S, Borisy A A, Stockwell B R, Keith C T, "Chemical combination effects predict connectivity in biological systems," Mol Syst Biol vol. 3, p 80, 2007; Kaufman A, Keinan A, Meilijson I, Kupiec M, Ruppin E, "Quantitative analysis of genetic and neuronal multi-perturbation experiments," PLoS Comput Biol vol. 1, e64, 2005).

Combinatorial perturbations can also be powerful application tools when rationally designed to achieve desired effects. For example, a combination of targeted drugs is considered a promising strategy to improve treatment efficacy, reduce off-target effects, and/or prevent evolutionary drug resistance. (See, for example, Borisy A A, Elliott P J, Hurst N. W, Lee M S, Lehar J, Price E R, Serbedzija G, Zimmermann G R, Foley M A, Stockwell B R, Keith C T, "Systematic discovery of multicomponent therapeutics," Proc Natl Acad Sci USA vol. 100, pp 7977-7982, 2003; Chou T C, "Theoretical basis, experimental design, and computerized simulation of synergism and antagonism in drug combination studies," Pharmacol Rev, vol. 58, pp 621-681, 2006; Keith C T, Borisy A A, Stockwell B R, "Multicomponent therapeutics for networked systems," Nat Rev Drug Discov vol. 4, pp 71-78, 2005; Komarova N, Wodarz D, "Drug resistance in cancer: principles of emergence and prevention," Proc Natl Acad Sci USA, vol. 102, pp 9714-9719, 2005).

With recent advances in molecular and computational technologies (e.g., targeted perturbation by small molecules, full-genome libraries of small RNAs, highly specific antibody assays, massive computer parallelization, and imaging techniques) there is intense interest in the investigational power of multiple perturbation experiments in a variety of biological systems. The inherent complexity of such experiments raises significant challenges in data analysis and an acute need for improving modeling approaches capable of capturing effects such as time-dependent responses, feedback effects and non-linear couplings.

Computer simulation of pathway models can be used to predict epistasis and other effects on cellular behavior only if such pathway models are well established means of predicting cellular behavior, i.e., if the pathways have been exhaustively tested with respect to their ability to predict experimental outcomes (see, for example, Lebar et al., 2007; Omholt SW, Plahte E, Oyehaug L, Xiang K, "Gene regulatory networks generating the phenomena of additivity, dominance and epistasis," Genetics vol. 155, pp 969-980, 2000; Segre et al, 2005). In many situations, however, observational data is available but a valid pathway is unknown or is incompletely tested against experiment.

SUMMARY OF THE INVENTION

Techniques are provided for modeling interactions in a living biological system, such as modeling signaling pathways.

In a first set of embodiments, a method includes determining multiple state variables and multiple perturbation variables. State variables y indicate relevant properties of a living biological system. Perturbation variables u indicate physical factors that might affect one or more of the relevant properties of the biological system. A measurable subset $\Omega$ of the state variables is also determined. A measureable variable of $\Omega$ is a cell state variable for which a value can be derived based on a measurement. Measurement-based values Y are received for the measurable variables in $\Omega$. Model constants are determined based on the measurement-based values Y. The model constants include a constant interaction factor $w_{ij}$ between a first state variable $y_i$ and a second state variable $y_j$. The model constants are determined so that a change in a value of $y_i$ over time depends, at least in part, on a non-linear transformation of a sum of a value of a perturbation variable $u_i$ that affects $y_i$ added to a sum of all non-zero values for a product of $w_{ij}$ and $y_j$ for all state variables. Model data is determined, which indicates the model constants, the plurality of state variables y and the plurality of perturbation variables u for a model that predicts a temporal change in $y_i$ based on values for the plurality of state variables y and for a perturbation variable $u_i$.

In another set of embodiments, a method includes receiving model data that includes values for a plurality of constant interaction factors $w_{ij}$. A set of initial state values is received for state variables y that indicate relevant properties of a living biological system. Also received is a set of trial values for perturbation variables u that indicate factors that might affect one or more of the relevant properties of the biological system. A change over time in a value for a particular state variable $y_i$ is determined based, at least in part, on a non-linear transformation of a sum of the trial value for the perturbation variable $u_i$ that affects $y_i$ added to a sum of all non-zero values for a product of $w_{ij}$ and $y_j$ over all state variables.

In another set of embodiments, a method for screening drugs for treating a biological system includes receiving a set of initial state values for multiple state variables y that indicate relevant properties of a living biological system. Also received is model data that includes values for multiple constant interaction factors $w_{ij}$ between pairs of state variables. A set of trial values is received for a set of one or more drugs that might affect one or more of the relevant properties of the biological system. A change over time in a value for a particular state variable $y_i$ is determined based, at least in part, on a non-linear transformation of a sum of the set of trial values that affect $y_i$ added to a sum of all non-zero values for a product of $w_{ij}$ and $y_j$ over all state variables in the plurality of state variables. Efficacy of the set of trial values for the set of one or more drugs in treating the biological system is determined based on the change over time in the particular state variable.

In some of these embodiments, it is determined whether the efficacy of the set of trial values for the set of one or more drugs exceeds a threshold value. If it is determined that the efficacy exceeds the threshold value, then selecting the set of one or more drugs for therapeutic use.

In other sets of embodiments, an apparatus or computer-readable storage medium is configured to cause one or more steps of the above methods to be performed.

BRIEF DESCRIPTION OF THE DRAWINGS

The present invention is illustrated by way of example, and not by way of limitation, in the figures of the accompanying drawings and in which like reference numerals refer to similar elements and in which:

FIG. 1 is a block diagram that illustrates perturbations to processes in a living cell.

FIG. 2 is a block diagram that illustrates an example network model for perturbations to processes in a living cell, according to an embodiment;

FIG. 3 is a block diagram that illustrates a structure matrix for interaction factors for the example network model of FIG. 2, according to an embodiment;

FIG. 5 is a flow diagram that illustrates at a high level an example method for modeling a living biological system with a non-linear network model, according to an embodiment;

FIG. 7 is a flow diagram that illustrates at a high level an example method for forming the non-linear network model, according to an embodiment;

FIG. 8 is a flow diagram that illustrates at a high level an example method for determining model constants for the non-linear network model, according to an embodiment;

FIG. 10A is a block diagram that illustrates an example vector of perturbation values for 21 experiments, according to an embodiment;

FIG. 10B is a block diagram that illustrates an example vector of observed values for the state variables for 21 experiments, according to an embodiment;

FIG. 11A and FIG. 11B are block diagrams comparing example measured values and example model output, according to an embodiment;

FIG. 14 is a block diagram that illustrates a computer system upon which an embodiment of the invention may be implemented.

DETAILED DESCRIPTION

Figure 4A:
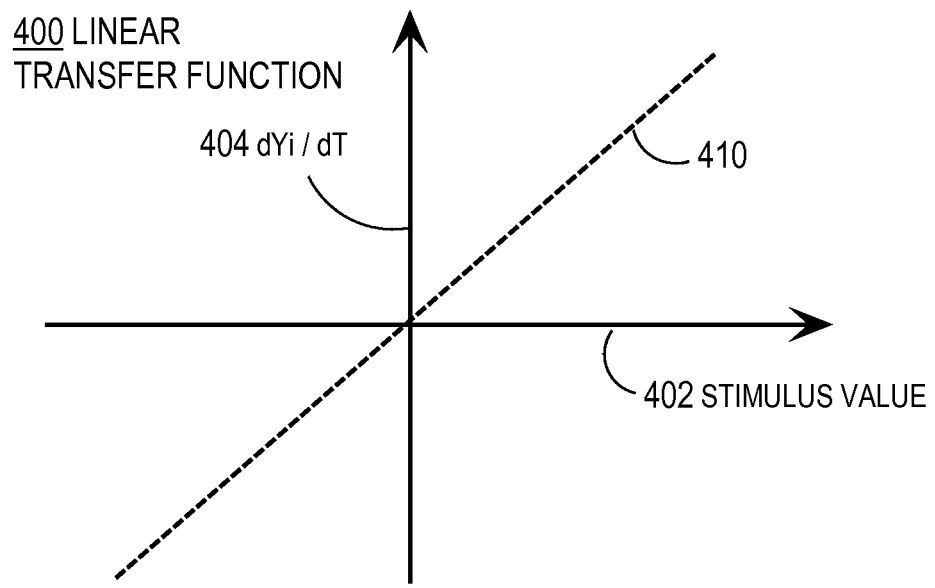
FIG. 4A is a graph that illustrates a linear transfer function.

Techniques are described for modeling living biological systems. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Some embodiments of the invention are described below in the context of modeling the response of breast cancer cells to drug treatment. However, the invention is not limited to this context, and includes modeling biological systems. As used herein, a biological system is a collection of one or more cells, including bacteria, viral infected cells, diseased or healthy cells, in vitro or in immortalized cell lines, e.g., transformed to divide and survive, at least temporarily, in culture, or one or more types of cells, such as found in tissue, organs and organisms. In various embodiments biological systems are modeled for treatment or other effects of externally controlled factors. In various embodiments the modeling is performed for (but not limited to) extending or evaluating known models/pathways, designing experiments to determine relevant state parameters or perturbing agents or both, to determine the specificity spectrum (list of percentage effect on intended and unintended targets) of a particular perturbing agent, to consider the effects of antibodies or of one or more varieties of RNA (e.g., siRNA, shRNA anti-miRNA) on state, to determine the effects of multiple different combinations of perturbing agents for designing novel drug combinations for any desired effect, to determine the effects of defined time protocols for the administration in sequence of any combination of perturbing agents for any desired effect, to detect regulatory differences between similar biological systems, to model and predict functional interactions between pre-existing genetic alterations and drug perturbations, to determine how to control behavior, to determine and design the effects of replacing regulatory modules in biological system in the context of cell or tissue engineering or synthetic biology, for the prevention or mitigation of environmental effects, or some combination of these.

1. Overview

FIG. 1 is a block diagram that illustrates perturbations to processes in a living biological system, such as a cell 190. The cell 190 includes internal processes and intermediate substances (intermediates) produced during those processes 192 represented by a revolving dashed circle in cell 190. The cell 190 also includes a cell membrane with receptors 194 for binding to molecules or families thereof. Such families of molecules that bind to receptors on a cell membrane or to molecules inside the cell are called ligands, drugs or, more generally, perturbation agents or perturbants.

Externally controlled factors called perturbing agents and modifications 120 affect one or more processes and intermediates of the cell, by binding to, penetrating or disrupting the cell membrane. Perturbing agents are naturally present outside the cell or are introduced externally and bind to macromolecules outside or inside the cells and affect the state of the cell over time. Perturbing modifications, such as genetic alterations, are changes in cellular molecules relative to some normal state of the cell or organ, e.g., defined by a healthy individual or by a population average. Example classes of perturbing agents and modifications are indicated by different symbols in FIG. 1, including small compounds or elements 122, ligands 124, small RNA 126 that passes readily through the cell membrane, genetic alterations 128 (sometimes accomplished by introducing genes via needle or through a molecular vector into the cell 190 or its nucleus, not shown), and other externally controlled physical processes 129, such as temperature change, pressure change, pH change, mechanical stress, acoustic waves, electromagnetic radiation (including light and X-rays), and particle radiation.

The results of introducing the perturbing agents or modifications 120 to the cell 190 are outcomes 140 that are observable, whether in a living cell (e.g., phenotype) or a denatured product of the cell (as the result of a chemical or physical analysis, e.g., using mass spectroscopy). Example classes of outcomes are indicated by different blocks in FIG. 1, including genetic transcripts 142 (mRNA transcribed by the cell 190 from endogenous cellular genes), phenotype 144 (e.g., cell shape, function or behavior, including death), or protein or protein fragment content distributions 146 (e.g., determined by analysis of a denatured cell).

FIG. 2 is a block diagram that illustrates an example network model 200 for perturbations to processes in a living biological system, according to an embodiment. The network model 200 includes nodes that each represents a different state variable 230. A state variable indicates one relevant property of a living biological system e.g., a molecule that might respond to a drug for treatment of breast cancer in an illustrated embodiment.

As used herein, a variable refers to a data type that can hold any one of multiple possible values appropriate for that type. The appropriate values depend on the data type. For example, a variable that indicates a particular molecule can hold any one of multiple values that represent a property of that molecule, such as its state or amount. In many embodiments, the variable is implemented as a location in a computer memory, as described in more detail below.

The nodes are collectively referenced herein as states y, e.g., states y 230 in FIG. 2. In general, there are a total of N states in y, each represented by $y_i$, where i is an index that is an element of the set of numbers from 1 to N (i∈1 to N). Thus y is an array of variables (also called a vector of variables, herein). In the example depicted in FIG. 2, N=12, and states y 230 includes state $y_1$ 231, state $y_2$ 232, state $y_3$ 233, state $y_4$ 234, state $y_5$ 235, state $y_6$ 236, state $y_7$ 237, state $y_8$ 238, state $y_9$ 239, state $y_{10}$ 240, state $y_{11}$ 241 and state $y_{12}$ 242.

The network model 200 also includes nodes that each represents a different perturbation variable. A perturbation variable indicates an externally controlled perturbation agent that might affect one or more of the relevant properties of the biological system, e.g., a drug for treatment of breast cancer in an illustrated embodiment. The perturbation nodes are collectively referenced herein as perturbations u, e.g., perturbations u 220 in FIG. 2. In general, there is a total of M perturbations in u, each represented by $u_k$, where k is an index that is an element of the set of numbers from 1 to M (k∈1 to M). Thus u is a vector of variables. In the example depicted in FIG. 2, M=5, and perturbations u 220 includes perturbation $u_1$ 221, perturbation $u_2$ 222, perturbation $u_3$ 223, perturbation $u_4$ 224 and perturbation $u_5$ 225.

Each perturbation is associated with at least one state called a target state. For purposes of illustration, the states and perturbations are indexed so that $u_k$, is associated with (e.g., targets) $y_i$, when k=i. When each perturbation targets only one state and N>M, then there is no perturbation associated with some states, e.g., there is no perturbation associated with $y_i$, for i>M. In FIG. 2, there is no perturbation associated with $y_i$, for i>5. The associations between perturbations $u_i$ and states $y_i$ for i≤5, are illustrated in FIG. 2 by input paths 229. In embodiments in which multiple perturbations target the same state, the symbol $u_i$ is intended to represent a vector of all the perturbations that target the state $y_i$.

The network model 200 includes edges connecting nodes. Each edge represents a different non-zero interaction between two nodes. A non-zero interaction indicates that the value for one state, called a source state, affects the time rate of change of a value for another state, called a destination state. The edges are collectively referenced herein as interaction factors w, e.g., interaction factors w 270 in FIG. 2. In general, there is a total of L interaction factors in w, each represented by $w_{i,j}$, where i is an index that indicates a destination state and j is an index that indicates a source state. Thus w can be represented as a two-dimensional array of interaction factors (also called a matrix, herein).

Unlike states y 230 and perturbations u 220, the interactions factors w 270 are constants for a particular network model, not variables. A positive value for $w_{i,j}$ indicates that the value for the destination state varies directly with the value for the source state (e.g., an increase in value for the source leads to an increase in value for the destination state) and the interaction is activating. A negative value for $w_{i,j}$ indicates that the value for the destination state varies inversely with the value for the source state (an increase in value for the source state leads to a decrease in value for the destination state) and the interaction is inhibitory. In FIG. 2, arrows representing interaction factors w 270 point from a source state to a destination state. Positive interaction factors are indicated by a solid triangular arrowhead. Negative interaction factors are indicated by an open circle arrowhead. For example, in network model 200, $w_{9,3}$ is positive and $w_{3,11}$ is negative.

Although there are $N^2$ possible interaction factors, in general only $L<N^2$ are non-zero. Preferably, L is much less than $N^2$. In the example depicted in FIG. 2, L=12, and is much less than $N^2$=144.

A subset of the states y represents properties that can be measured. The states that can be measured are collectively referenced herein as measurable states Ω, e.g., measurable states Ω 250 in FIG. 2. The relationship between the states y 230 and the measurable states Ω 250 are indicated in FIG. 2 by dashed arrows. In general, there is a total of O≤N measurable states Ω, each represented by $\Omega_p$ where p∈(1 to O). FIG. 2 depicts 3 measurable states represented by $\Omega_1$ 251, $\Omega_2$ 252 and $\Omega_3$ 253. Alternatively, the subset can be represented by a set $I_\Omega$ of values for index i that indicate measurable states. For example, in FIG. 2, the states that are members of the subset Ω, are indicted by indices i∈(8, 10, 11) and can be represented by i∈$I_\Omega$ where $I_\Omega$=(8, 10, 11).

Although FIG. 2 depicts 5 perturbations, each affecting only one of 12 states connected by 12 interaction factors to produce 3 measurable states for purposes of illustration, in various other embodiments a network model includes a different number of perturbations, or each affects a different number of a states, or there is a different number of states or interaction factors or measurable states, or some combination.

FIG. 3 is a block diagram that illustrates a structure matrix (S) 300 for interaction factors for the example network model of FIG. 2, according to an embodiment. The structure matrix 300 includes N=12 rows and N=12 columns and indicates the non-zero interaction factors. The columns of S are labeled by column numbers j 302 that indicate a source state. The rows are labeled by row numbers i 304 that each indicates a destination state. A structure matrix element associated with a particular row and a particular column indicates whether the interaction factor corresponding to that particular row and column is non-zero. A zero at a matrix element indicates the corresponding interaction factor is zero and a 1 indicates that the interaction factor is non-zero. For example, structure matrix element 310 for row 12 column 6 is zero, indicating that $w_{12,6}$ is zero. In contrast, structure matrix element for row 12 column 10 is one, indicating that $w_{12,10}$ is non-zero.

The cell 190 is modeled as a natural system with inputs=perturbations u and outputs=measurable states Ω. The time behavior of the state of the system is often described by a first order differential equation of the form given by Equation 1.

$$dy/dt = f\{y(t), u(t)\} \quad (1)$$

where y(t) is the setoff values for the state vector y at time t, u(t) is the set of values for the state vector u at time t, $f$ is a transfer function, and dy/dt is the time rate of change of the state vector y at time t. In network models, like 200, at each time t, the values of at least some elements of the vector y affect one or more other elements of the vector y, as given by the interaction factors w, before being input to the transfer function $f$.

Prior models of cell systems that can be characterized as network models, like model 200 defined above, have used a linear transfer function $f$ to combine all the contributions (called stimuli) to a particular cell state at a particular time. FIG. 4A is a graph 400 that illustrates a linear transfer function. The horizontal axis 402 indicates total value of stimulus equal to the sum of the individual contributions. The vertical axis 404 indicates a net time rate of change $dy_i/dt$ of values for a particular state variable $y_i$. The linear transfer function 410 gives the time rate of change as a function of the stimulus for an activating stimulus. (For an inhibitory stimulus, the line of transfer function would slope down). The more the stimulus value increases the greater is the response.

For example, linear transfer functions are used to construct transcriptional network models by Tegner J, Yeung M K, Hasty J, Collins J J, "Reverse engineering gene networks: integrating genetic perturbations with dynamical modeling," *Proc Natl Acad Sci USA* vol. 100, pp 5944-5949, 2003; Xiong M, Li J, Fang X, "Identification of genetic networks," *Genetics* vol. 166, pp 1037-1052, 2004; and di Bernardo D, Thompson M J, Gardner T S, Chobot S E, Eastwood E L, Wojtovich A P, Elliott S J, Schaus S E, Collins J J, "Chemogenomic profiling on a genome-wide scale using reverse engineered gene networks," *Nat Biotechnol* vol. 23, pp 377-383, 2005.

The inventors have noted that such a combination fails to provide a full range of realistic behavior. Linear transfer functions are appropriate for independent, uncoupled perturbation effects, such as linear dose-response relationships with no drug interactions. However, linear transfer functions fail to provide switch-like, synergistic, antagonistic or saturation behavior sometimes observed with interactions resulting from the application of drugs in combination. Such observations include metabolic systems with Michaelis-Menten kinetics, transcriptions networks, and complex gene knockout effects, including epistasis effects. Epistasis refers to interactions among genes, such that a combination of active genes gives a result different from the sum of their behavior when individually expressed. To model such effects with linear transfer functions, bounds on the reaction rates are introduced in metabolic flux networks and bounds on transcription rates are introduced in transcriptional networks. See, for example, Fell D A, Small J R, "Fat synthesis in adipose tissue. An examination of stoichiometric constraints," *Biochem J* vol. 238, pp 781-786, 1986; Edwards J S, Palsson B O, "Robustness analysis of the *Escherichia coli* metabolic network," *Biotechnol Prog* vol. 16, pp 927-939, 2000; Seagre et al., 2005; and Deutscher D, Meilijson I, Kupiec M, Ruppin E, "Multiple knockout analysis of genetic robustness in the yeast metabolic network," *Nat Genet* vol. 38, pp 993-998, 2006; Omholt et al., 2000; and Lehar et al, 2007). Such bounds are established by a human analyst and may be non-optimal.

Figure 4B:
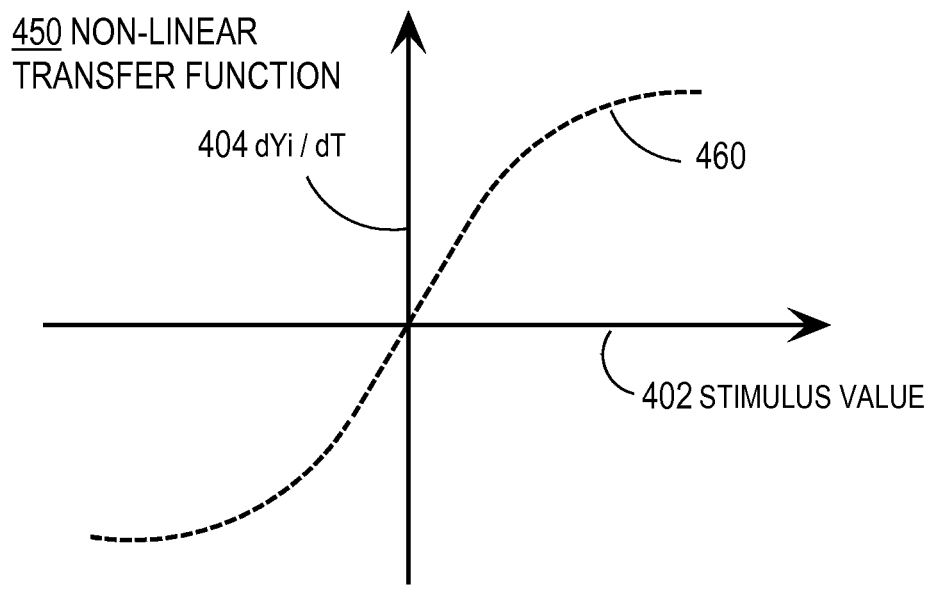
FIG. 4B is a graph that illustrates an example non-linear transfer function, according to an embodiment.

According to the preferred embodiments, all the contributions to a particular state are combined non-linearly to allow for non-linear interactions frequently observed in biological systems, as described above. FIG. 4B is a graph 450 that illustrates an example non-linear transfer function, according to an embodiment. The horizontal axis 402 and vertical axis 404 are as described above for FIG. 4A. The non-linear transfer function 460 gives the time rate of change as a function of the total stimulus for an activating stimulus. (For an inhibitory stimulus, the transfer function would be reflected about horizontal axis 402). In some stimulus ranges, e.g., near the crossing with axis 404, the rate change is large for a small change in stimulus, simulating synergy. In some stimulus ranges, e.g., far from the axis 404, even large changes in stimulus value produce small or no change in rate. At the left edge of graph 450 the behavior simulates switch on behavior, as moving from left to right with increasing stimulus, the response goes from little or no response to a significant noticeable response. At the right edge of graph 450, the behavior simulates saturation behavior, as moving from left to right with increasing stimulus, the response goes from significant noticeable response to little or no response.

In the illustrated embodiments, the time rate of change of values for the state vector y is given by Equation 2.

$$dy_i/dt = \beta_i \phi_i \{\Sigma_{j=1,N} [w_{i,j} y_j(t)] + u_i(t)\} - \alpha_i y_i(t), \text{ for } i=1,N \quad (2)$$

where $\alpha_i$ is a model relaxation constant that represents the tendency of the state to return to its native value; and $\beta_i > 0$ is a response proportionality constant; and $\phi_i$ is a non-linear transfer function. The non-linear transfer function $\phi_i$ is chosen to be capable of capturing both switch-like behavior (from little response to great response) and bounded reaction rates (constant maximum response) or synergistic behavior (larger than average response). Examples of such functions include sigmoid functions, piecewise linear approximations of sigmoid functions, trigonometric approximations of sigmoid functions, and biochemically motivated approximations of sigmoid functions (such as Hill or Michaelis-Menten equations).

In various embodiments of the invention, a model based on Equation 2, or portions thereof, is formed or used to model living biological systems, or both.

2. Method of Using a Non-linear Model of a Living Biological System.

FIG. 5 is a flow diagram that illustrates at a high level an example method for modeling a living biological system with a non-linear network model, according to an embodiment. Although steps in FIG. 5 and subsequent flow charts, FIG. 7 and FIG. 8, are shown in a particular order for purposes of illustration, in other embodiments, one or more steps may be performed in a different order or overlapping in time, in series or in parallel, or one or more steps may be omitted or added, or changed in some combination of ways.

In step 510, model data is received. The model data includes data that indicates the N state variables, the measurable subset of state variables, the perturbations variables, and the associations among the perturbation variables and one or more of the state variables. The model data includes constant values for the non-zero interaction factors $w_{ij}$. In some embodiments the model data includes constant values for the response proportionality constants $\beta$ and model relaxation constants $\alpha$ for one or more state variables.

In some embodiments, the model data includes normalization rules for supplying values for each state variable and each perturbation variable. In some embodiments, a value for a natural state (also called a wild or unperturbed state) for the living biological system is normalized to equal zero. In some embodiments, the wild state is a healthy state; and, in some embodiments, the wild state is a diseased state or damaged state. For example, in some embodiments values for the state variables are normalized according to Equation 3a.

$$y_i = \log_2(y_i'/y_{0i}) \qquad (3a)$$

where $y_i'$ is the un-normalized value for the particular state variable $y_i$, and $y_{0i}$ is the wild value, and $\log_2$ is the logarithm to the base 2. Every factor of two for the ratio $y_i'/y_{0i}$ increments or decrements the value of $y_i$ by 1.

In some embodiments, values for all the perturbation variables are normalized so that a value of one indicates the recommended dose or amount for the corresponding perturbation, if any. For example, in some embodiments, values for the perturbation variables that refer to drug concentrations are normalized according to Equation 3b.

$$u_i = u_i'/ED_{90} \qquad (3b)$$

where $u_i'$ is the un-normalized value for the particular perturbation variable $u_i$ and $ED_{90}$ is the effective dose of a drug for 90 percent of the population. Since a perturbation can be set to zero, a normalization using a logarithm is not appropriate. The normalizations represented by Equation 3a and Equation 3b help keep the value of total stimulus (argument of $\phi_i$ in Equation 2) close to the range from −1 to +1, where many sigmoid-type functions change most rapidly from near-minimum values to near-maximum values.

Any method may be used to receive this model data. For example, in various embodiments, the model data is included as a default value in software instructions, is received as manual input from a system administrator on the local or a remote node, is retrieved from a local file or database, or is sent from a different node on a communications network, either in response to a query or unsolicited, or the data is received using some combination of these methods.

In some embodiments, step 510 is accomplished in response to forming the model, as described in more detail below with reference to FIG. 7.

In step 580, values for the state variables are received that indicate an initial state of the biological system, e.g. the cell. These values are called the initial state values. Any method may be used to receive these values, as described above for model data. In some embodiments, the initial values indicate the natural state (also called the wild or unperturbed state) for the living biological system. In some embodiments the wild state is a healthy state; and in some embodiments the wild state is a diseased state or damaged state. In some embodiments, values for all the state variables are normalized so that a value of zero indicates the wild state and step 580 comprises setting $y_i = 0$ for all i∈(1 to N).

In step 582, values for the perturbation variables are received that indicate perturbations to be tried on the biological system. These values are called the trial perturbation values. In some embodiments, the trial perturbation values are specified by a particular accepted or proposed protocol for treating the system. In some embodiments, the trial perturbation values are simply candidate values for a proposed new treatment, which values will be adjusted based, at least in part, on model results obtained in step 598, described below.

In step 584, a change in state values with time, for at least one state variable $y_i$, is determined based on $\phi_i \{\Sigma_{j=1,N} [w_{i,j} y_j(t)] + u_i(t)\}$ from Equation 2. In some embodiments the change in state values includes some or all the additional terms of Equation 2, including using constants $\alpha_i$ and $\beta_i$. For example, in some embodiments, the sigmoid function $\phi_i$ is the same for all state variables and is given by Equation 2c.

$$\phi_i(x) = \tanh(2x) \text{ for all } i \in (1 \text{ to N}) \qquad (3c)$$

In step 586, it is determined whether there is another state variable at index i+1 to determine a value change. If so, control passes to step 588. In step 588, the index is incremented and control passes back to step 584. If the change has been determined for all i of interest, so that there is not another state, control passes from step 586 to step 590.

In step 590, it is determined whether there is another time step at which to determine a value change. If so, control passes to step 592. In step 592, the time is incremented and the index is reset to the first index of interest, and control passes back to step 582. If it is determine in step 590 that there is not another time step, then control passes to step 594.

In step 594, it is determined whether the resulting final values for the state variables are desired. If so, control passes to step 598. In step 598 one or more of the final values for the states is used for a particular purpose, for example to predict the result of a given target perturbation or to specify the perturbations to achieve a target behavior. Other possible applications include the discovery of regulatory interactions, the design of targeted combination therapies, and the engineering of molecular biological networks.

If it is determined in step 594 that the final values are not a desired result, such as a target behavior for the biological system represented by target values for the measurable states $\Omega$, then control passes to step 596. In step 596, the time and index are reset and a number, called a trial number that indicates the number of trial perturbations attempted, is incremented. Control then returns to step 580 to input the initial values for the states and, subsequently, to step 582 to receive the trial perturbation values for the next trial.

Figure 6A:
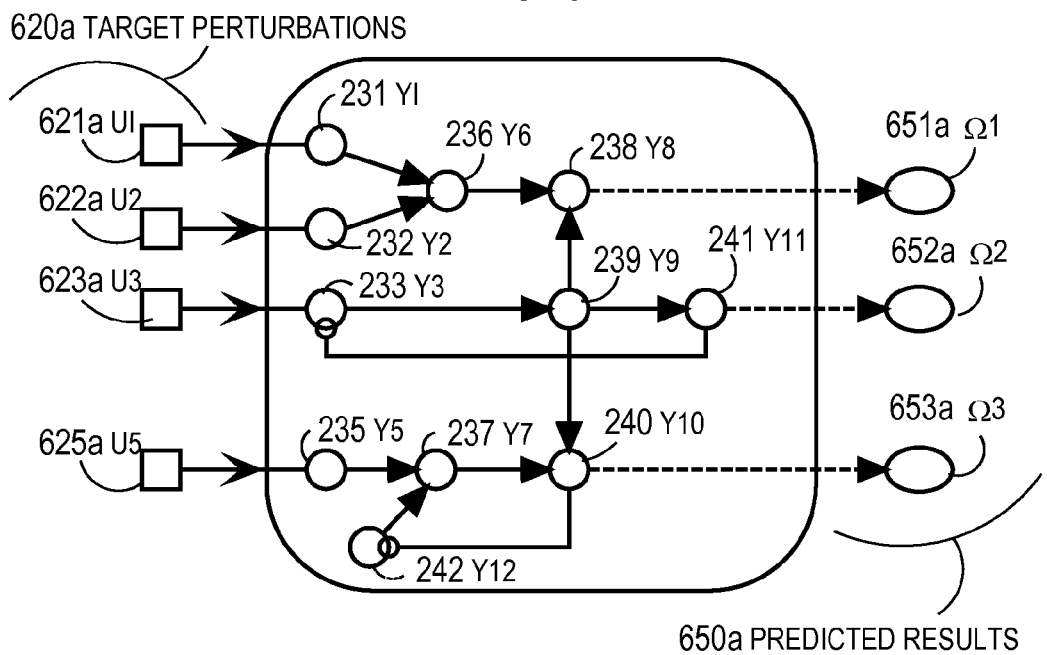
FIG. 6A is a block diagram that illustrates an example type of use of the network model of FIG. 2, according to an embodiment.

FIG. 6A is a block diagram that illustrates an example type of use of the network model of FIG. 2, according to an embodiment. In this embodiment, the perturbations are known and the results are unknown. For example, known perturbations include the therapeutically effective prescribed doses of several drugs used to treat the modeled by the state variables 230 and interactions 270 described above with reference to FIG. 2. The known values for the perturbations are called target perturbations 620a and include values for target perturbation $u_1$ 621a, target perturbation $u_2$ 622a, target perturbation $u_3$ 623a, and target perturbation $u_5$ 625a. Because perturbation $u_4$ did not affect the measurable states 250, it is excluded from the target perturbations 620a. As a result of applying the target perturbations 620a to a wild state, a set of resulting values for the measurable states are predicted. The predicted values for the measurable states are called predicted results 650a and include values for predicted result $\Omega_1$ 651a, predicted result $\Omega_2$ 652a, and predicted result $\Omega_3$ 653a.

Examples of uses with target perturbations and predicted results include: 1] determining the effects of certain drug combinations; 2] determining what perturbations to introduce and states to measure when designing experiments, such as experiments for combinatorial therapies or experiments to verify or refute a particular model; 3] determining the specificity spectrum of a perturbing agent (e.g., a list of percentage change in intended and unintended targets of a particular perturbing agent); and 4] predicting the effect of genetic engineering, such as replacing a regulatory module in a cell with a different, externally introduced module.

Figure 6B:
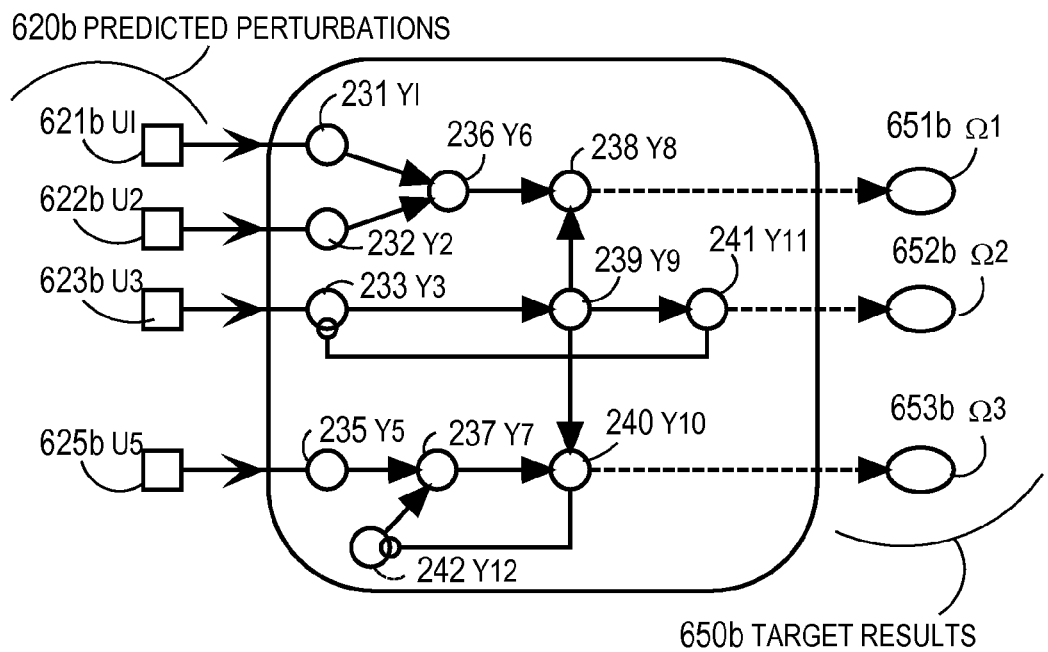
FIG. 6B is a block diagram that illustrates a different example type of use of the network model of FIG. 2, according to an embodiment.

FIG. 6B is a block diagram that illustrates a different example type of use of the network model of FIG. 2, according to an embodiment. In this embodiment, the desired results are known and the needed perturbations are unknown. For example, known desired results include the growth, growth rate or death of the cell modeled by the state variables 230 and interactions 270 described above with reference to FIG. 2. The known values for the measurable states are called target results 650b and include values for target result $\Omega_1$ 651b, target result $\Omega_2$ 652b, and target result $\Omega_3$ 653b. The model is run several times, as indicated in steps 594 and 596 in FIG. 5 described above, using trial values that are varied until the desired result is obtained. Often the trial perturbation values are adjusted optimally for the next trial based on associating changes in the perturbation values with changes in the deviations of the predicted results from the desired results. The resulting, but initially unknown, values for the perturbations are called predicted perturbations 620b and include values for predicted perturbation $u_1$ 621b, predicted perturbation $u_2$ 622b, predicted perturbation $u_3$ 623b, and predicted perturbation $u_5$ 625b. Because perturbation $u_4$ did not affect the measurable states 250, it is excluded from the predicted perturbations 620b. As a result of applying the predicted perturbations 620b to a wild state, the set of desired target values are produced for the measurable states.

Examples of uses with target perturbations and predicted results include: 1] determining controls for certain biological system behavior; 2] determining the perturbations to cause a particular result; and 3] designing experiments that produce results that are large enough to be detected.

In some embodiments, the inputs and outputs are both known, and are used to determine the interaction factors w and other constants of the model (e.g., the internal wiring of the biological system), as described in more detail in the following section. Examples of uses of this mode are: 1] evaluate a candidate model; 2] interpret the internal processes of the biological system, 3] to evaluate and extend currently accepted signaling pathways, as described in more detail in a subsequent section; and 3] identifying target states for interesting drugs or compounds that have a desirable effect.

In some embodiments, a model based on Equation 2, or portions thereof, is used to test the efficacy of a combination of drugs. Efficacy is any measure that increases with increased effectiveness to produce a desired result, such as toxicity to diseased tissue, and decreases with increased production of an undesirable result, such as toxicity to non-diseased tissue. If efficacy is above a certain threshold, then the combination of drugs is considered for therapeutic use, such as for clinical trials. If the drug combinations pass clinical trials, then the drug combinations are used to treat patients who have the diseased tissue.

3. Method of Forming a Non-linear Model of a Living Biological System.

FIG. 7 is a flow diagram that illustrates at a high level an example method 700 for forming the non-linear network model, according to an embodiment. Method 700 uses known perturbations and observed results to derive the model constants.

In step 710, a set of state variables y that indicate relevant properties of a living biological system is determined. Any method may be used to identify the state variables. In some embodiments, the state variables are the targets for an array of perturbations to be tried as well as the properties of interest that can be measured, the latter including growth, division or death in various embodiments. In some embodiments, additional properties, such as intermediaries, suspected of playing a role are added to the set of state variables. It is preferable to keep the list of cell state variables as small as possible to explain the cell process being modeled, in order to allow for a more robust solution in some following steps, explained in more detail below. There are at least hundreds of thousands of components and processes in a cell or other biological system, from which a person of skill in the art can select the most important dozen or so for modeling a particular process under investigation.

In some embodiments, data indicating the selected state variables are stored as a portion of model data. For example, a state variable array of size 3×N is filled with N names of the state variables, the N corresponding names for units of measurement, and N reference values for the wild values $y_{0i}$ used during normalization with Equation 3a. In some embodiments, step 710 comprises receiving the state variable array.

In step 720, a set of perturbation variables u that indicate externally controlled factors that might affect values for one or more associated state variable is determined. Any method may be used to determine the perturbation variables. For example, perturbation variables are selected for factors expected to target one or more of the state variables. In some embodiments, one or more perturbation variables are selected based on the commercially available MIT "connectivity map" (cmap) database. The cmap database contains the results of administering various amounts of more than 164 distinct small-molecule perturbants, selected to represent a broad range of activities, and including U.S. Food and Drug Administration (FDA)—approved drugs and nondrug bioactive "tool" compounds, on mRNA expression of about 33,000 different genes in several different human lines. A total of 564 gene-expression profiles were produced, representing 453 individual instances (i.e., one treatment and vehicle pair). The genes on the array are rank-ordered according to their differential expression relative to controls (J. Lamb, et al., *Science*, 29 Sep. 2006, Vol. 313. no. 5795, pp. 1929-1935; and *Nature Reviews Cancer* 7, 54-60, January 2007).

In some embodiments, data indicating the selected perturbation variables are stored as a portion of model data. For example, a perturbation variable array of size 4'M is defined with M names of the perturbation variables, the M corresponding names for units of measurement, M reference values for the effective amount of the perturbation (e.g., $ED_{90}$) used during normalization with Equation 3b, and M lists of indices for one or more state variables affected by a corresponding perturbation variable. In an illustrated embodiment, the association is simplified for purposes of illustration, so that perturbation $u_k$ is associated with state $y_i$ only for k=i; and the perturbation variable data array is only 3×M in size, relying on an implied association and leaving out explicit lists of associations. In some embodiments, step 720 comprises receiving the perturbation variable array.

In step 730, a subset of the state variables that are measureable is determined. These variables are called herein the measurable state variables Ω. Any method may be used to determine the subset. For example, the state variables are selected in step 710 with a knowledge of which variables are measurable. In an illustrated embodiment, the subset of Ω is indicated by a list of indices $I_Ω$ for the state variables that are measureable. In some embodiments, measurable list data indicating $I_Ω$ are stored as a portion of model data. In some embodiments, step 730 comprises receiving the measurable list data.

As stated above, model formation or evaluation is performed in embodiments in which values for both the inputs u and measurable outputs Ω are known. The remaining steps 740, 750 and 790 produce the model based on the known input and output values.

In step 740, data is received that indicates values for perturbation variables u and resulting measurement-based values for subset Ω for each of one or more experiments. The matched set of values for u and values for Ω are called an experimental pair. The data may be obtained from publications or produced by additional experiments. Any method may be used to receive this data, as described above for receiving model data.

In step 750 the values of one or more constants for Equation 2 is determined for each state i across all experiments. By virtue of Equation 2, the temporal change in value of state $y_i$ depends on $α_i$ and the product of $β_i$ and a non-linear transform of the sum of the stimuli. The sum of the stimuli is given by a sum of the associated perturbation values $u_i$ added to a sum of non-zero products of the $w_{ij}$ and $y_j$ for all j. A method for determining the constants according to some embodiments that minimize a value of an error function is described in more detail below with reference to FIG. 8. In some embodiments, an a priori determination is made to set $α_i=1$ or $β_i=1$, or both, or equal to other constant values, for all i; and further determination of α or β, or both, is omitted.

In step 790, model data is determined for describing a particular model to be used, e.g., in step 584 described above. In some embodiments, the model data includes the state variable array, the perturbation variable array, the measurable list data, and model constants w, α, β for all state variables, for each of one or more models. In some embodiments, all the models with an error function value below a particular error threshold value are included in a set of best models, and the variables and constants for each of the best models are stored in the model data.

In some embodiments, during step 790, state variables or perturbations or both that appear to have no significant role (e.g., $y_x$ that is not measurable, such that $w_{ix}=0$ for all i) are dropped from the data array of state variables and the data array of perturbation variables, and the values of N or M are reduced accordingly.

In some embodiments, step 790 includes splicing together the $w_{ij}$ from multiple models from one or more different types of living systems. For example, more complex models, e.g., for collections of different types of cells, are generated by combining several simpler models for a particular type of living cell. In some other embodiments, a model for predicting the effects of a particular cell alteration is formed by inserting a partial signaling pathway (e.g., a particular regulatory module represented by a subset of the state variables, $y_i$) deduced from one cell type into a different type of cell. This has the effect of replacing a different partial signaling pathway (e.g., a different regulatory module) with a desired change in properties of the target cell as determined from the model.

FIG. 8 is a flow diagram that illustrates at a high level an example method 800 for determining model constants for the non-linear network model of living biological systems, according to an embodiment. Thus method 800 is a particular embodiment of step 750, described above.

In step 802, data indicating a priori favored non-zero interactions are received. Any method may be used to receive this data, as described above for model data. For example, in some embodiments, step 802 involves receiving accepted interaction data that indicates a list $I_{accepted}$ of one or more index pairs (i,j) that identify non-zero interactions $w_{ij}$ in known or accepted pathways. Step 802 is included in some embodiments in which a model is being formed to test whether a known or accepted pathway can be extended. In some embodiments no particular interaction is favored a priori, and step 802 is omitted (or the list $I_{accepted}$ is empty).

In step 804 a seed structure matrix $S_{seed}$ with a limited number of elements equal to one, indicating non-zero interaction factors $w_{ij}$, is determined. A structure matrix S has a value 1 at elements that have a non-zero interaction factor, $w_{ij}$, and a zero otherwise, as shown for example in FIG. 3, described above. For example, in some embodiments, in an initial $S_{seed}$, the elements $S_{ij}=1$ for the (i,j) pairs in the list $I_{accepted}$, and $S_{ij}=0$ otherwise. In some embodiments, such as embodiments in which there is no known or accepted non-zero interactions, $S_{ij}=0$ for all (i,j) pairs. In some embodiments, $S_{seed}$ is set equal to the structure matrix for a previously developed model.

According to some embodiments, determining the value for the model constants further comprises minimizing an error function for each of multiple structures for the model, wherein each structure adds a limited increment of non-zero interaction factors $w_{ij}$ to a set of seed structures. Each structure in the seed set has a limited number of non-zero interaction factors $w_{ij}$. In step 810, a set of one or more candidate structure matrices $S_c$ is generated from the seed structure matrix $S_{seed}$ by changing a limited number of elements in $S_{seed}$ for each of a number C of candidate models. In some embodiments, the change involves toggling a value at an element of $S_{seed}$ (so that a zero becomes a one and a one becomes a zero) at a limited number of randomly selected locations. In some embodiments, the change involves toggling a value at one deterministically defined different element of $S_{seed}$ (so that a zero becomes a one and a one becomes a zero) for each candidate matrix $S_c$. In an illustrated embodiment that seeks to find the minimum number of interactions that fit the experimental observations well, for which every element in an initial $S_{seed}$ is equal to zero, step 810 comprises generating a set of candidate structure matrices $S_c$ that each differs from a current $S_{seed}$ by one additional element equal to 1 (i.e., one additional non-zero interaction). In such embodiments, with every element of an initial $S_{seed}$ equal to zero, there are $C=N^2$ candidate structure matrices $S_c$, each with a different single element equal to 1 and all the remaining elements equal to 0. In some embodiments, all interactions are considered two way in the candidate structure matrices $S_c$, so that each matrix $S_c$ is symmetric about its diagonal and the candidates are constructed in just one diagonal portion of the matrix $S_c$.

In step 820, an initial set of values is generated for the non-zero interaction factors $w_{ij}$ and $\alpha$ and $\beta$ for all state variable $y_i$, i=1 to N. In an illustrated embodiment, the initial values are $w_{ij}=S_{ij}$, $\alpha_i=1$ and $\beta_i=1$, for i=1 to N and j=1 to N. Current values for the constants are set equal to the initial values.

In step 830, one of the experiments, called the current experiment, is considered. For the current experiment, predicted values $Yp_i$ for the subset $\Omega$ (=$y_i$, $i \in I_\Omega$) are determined based on the current values for the constants and initial values for state variables y appropriate for the experiment. For example, in some embodiments normalized using Equation 3a, the initial values for the state variables y are the wild values $y_i=0$ for all i. Deviations between the predicted normalized values $Yp_i$ ($i \in I_\Omega$) and the actually measured normalized values $Y_i$ ($i \in I_\Omega$) are determined. Any method may be used to define the deviations. In an illustrated embodiment, the deviations are defined as the sum of squares error, $E_{SSQ}$, according to Equation 4a.

$$E_{SSQ} = \Sigma i \epsilon I_\Omega (Y_i - Yp_i)^2 \tag{4a}$$

In step 840, it is determined whether the deviation is minimized (e.g., sufficiently small) for the current experiment. Any method may be used to determine if the deviation is sufficiently small. For example, in some embodiments, the deviation is considered sufficiently small if successive deviations resulting from two successive estimates of the constants differ by less than a small constant (e.g., 0.00001). In some embodiments, the deviations are considered minimized after one pass through an error-minimization integration, as described below for step 842.

If it is determined in step 840 that the deviation is not minimized, control passes to step 842 to determine changes in the constants to reduce the deviations. Any method may be used. In some embodiments, a gradient descent method is used to determine changes in the constants based on the change in error observed by the last two sets of values for the constants. For fixed values of $\alpha$ and $\beta$, the gradient descent method for determining changes in the interaction factor constants is expressed by Equation 4b.

$$dw_{ij}/d\tau = -\eta_i dE_{SSQ}/dw_{ij} \tag{4b}$$

where $\tau$ indicates number of successive estimates for the model constants, and $\eta$ is a number less than one that sets a speed for the method to converge on a solution. Equation 4b indicates that the desired change in the estimate for the model constant $w_{ij}$ is inversely proportion to the change in error $E_{SSQ}$ associated with the most recent change in the estimate for the model constant. If the error decreases, the next change is in the same direction as the previous change; if the error increases, the next change is in the opposite direction. Equation 4b has been applied, for example, by Pineda F J, "Generalization of back-propagation to recurrent neural networks," *Phys Rev Lett* vol. 59, pp 2229-2232, 1987.

In an illustrated embodiment, the method of Pineda is extended to include adjusting estimates of $\alpha$ and $\beta$, according to D'haeseleer P, Liang S, Somogyi R, "Genetic network inference: from co-expression clustering to reverse engineering," *Bioinformatics* vol.16: 707-726., 2000. This gives equations 5a through 5e, which defines changes in the model constants in terms of a parameter z. A steady state approximation is expressed by Equation 5a, which is Equation 2 without time dependent values of $y_i$ and $u_i$, so that $y_i$ changes with successive estimates $\tau$. In the following, the first derivative of the non-linear transform function $\phi_i$ is represented by $\phi_i'$.

$$dy_i/d\tau = \beta \phi_i \{\Sigma_{j=1,N}[w_{i,j} y_i] + u_i\} - \alpha_i y_i, \text{ for i=1,N} \tag{5a}$$

Error back-propagation is expressed by Equation 5b, which introduces the parameter $z_i$ for each state variable $y_i$.

$$dz_i/d\tau = \beta_i \Sigma_{n=1,N}(W_{n,i} Z_n \phi_n' \{\Sigma_{j=1,N}[W_{n,j} y_n] + u_n\}) - \alpha_i z_i + (Y_i - Y_i'), \text{ for i=1,N} \tag{5b}$$

The w update is then determined by Equation 5c.

$$dw_{ij}/d\tau = \eta \phi_i' \{\tau_{k=1,N}[w_{i,k} Y_k] + u_k\} Z_i y_j - S_{ij} w_{ij} \tag{5c}$$

The $\beta$ update is then determined by Equation 5d $$d\alpha_i/d\Sigma = -\Theta z_i y_j \tag{5d}$$

The $\beta$ update is then determined by Equation 5e $$d\beta_i/d\Sigma = -\Theta Z_i \phi_i \{\Sigma_{j=1,N}[W_{i,j} Y_j]\} \tag{5e}$$

Equations 5a though 5e are integrated numerically for each of multiple steps $\tau$ to give updates for the model constants $w_{ij}$, $\alpha_i$ and $\beta_i$. At each step $\tau$, the value of $y_i$ is updated using Equation 5a and then used in Equations 5b through 5d. Control passes to step 830 to evaluate the predicted values for the current experiment again, this time using the updated values for the model constants.

If it is determined in step 840 that the error is minimized, then final values for the model constants that minimize the deviations have been obtained for the current experiment; and control passes to step 850. In step 850, it is determined whether there is another experiment for which to determine constants. If so, control passes to step 852 to increment the current experiment to the next experiment. Control then flows back to step 830 and following steps to determine the model constants that minimize the deviations for the next experiment that is now current.

If it is determined in step 850 that there is not another experiment, then control passes to step 854. In step 854, the multiple versions of the constants from the different experiments are combined. Any method may be used to combine the constants determined from the different experiments. For example, in some embodiments, the model constants are combined using online learning with momentum, e.g., as described in Duda R O, Hart P E, Stork D G, Pattern Classification Wiley-Interscience Publication, John Wiley & Sons, Inc, New York, N.Y., 2000.

Step 854 includes determining a total error for the current structure. The total error includes a contribution that reflects the complexity of the current structure in order to favor less complex structures. The total error function grows with a number of non-zero interaction factors. For example, in an illustrated embodiment, a total error, $E_{TOTAL}$ is determined according to Equation 6a and Equation 6b.

$$E_{TOTAL} = E_{SSQ} + \lambda E_{STRUCT} \tag{6a}$$

where $$E_{STRUCT} = \Sigma_{i,j} |w_{ij}|^0 = \Sigma_{i,j} S_{ij} \tag{6b}$$

This definition of $E_{STRUCT}$ is equivalent to the $l^0$ norm for a matrix of interaction values $w_{ij}$. In other embodiments other measures of the complexity of the structure are used, such as norms of higher order than zero, such as a $l^1$ norm. $E_{SSQ}$ is determined by the sum of square deviations between the measured values Y and predicted values Yp using the combined model constants for all experiments.

$E_{STRUCT}$ is justified because less complex models are considered more probable. A Baysian rationale for this definition of $E_{TOTAL}$ is based on the following considerations. If P(M|D) denotes the posterior probability for a model M given the experimental data D and P(M) denotes the prior probability of a particular model, and P(D|M) is the data likelihood, then Bayes formula states that log P(M|D)=log P(D|M)+log P(M)−log P(D)

The last term is independent of model and can be disregarded. If a normal distribution error is assumed, then log(P(D|M)) is proportional to $-E_{SSQ}$. This follows from the definition of a normal distribution. The remaining term, log(P(M)), corresponds to $-E_{STRUCT}$. Hence, with this interpretation, minimizing $E_{TOTAL}$ is structurally close to maximizing P(M|D).

In some embodiments, the interaction factors that coincide with known or accepted interactions, received in step 802, are not used to increase the total error. In such embodiments, $E_{STRUCT}$ is reduced by the accepted non-zero interaction factors. Thus, the error function decreases for each non-zero interaction factor $w_{ij}$ that is desired to conform to an accepted pathway. For example, $E_{STRUCT}$ is defined as expressed in Equation 6c.

$$E_{STRUCT}=\Sigma_{i,j}S_{ij}-\Sigma_{i,j\in Iaccepted}S_{ij} \quad (6c)$$

Recall that $I_{accepted}$ is a set of i,j values associated with known or accepted interactions.

Control then passes to step 860 to determine whether there is another candidate structure to consider. If so, control passes to step 862. In step 862, the current experiment is reset to the first experiment and control passes back to step 820 to set initial values for the non-zero interaction factors for the new structure. The subsequent steps 830 to 854 then determine the combined constants across all experiments for the new current structure.

If it is determined in step 860 that there is not another candidate structure, then control passes to step 870. In step 870 the best probable structure is determined based on the total error ($E_{TOTAL}$). As seen in Equation 6a, 6b and 6c, the $E_{TOTAL}$ includes a penalty $E_{STRUCT}$ for structure size ($l^0$ norm) that is reduced for accepted interaction factors indicated by $I_{accepted}$. Any method may be used to determine the best model or models based on $E_{TOTAL}$. In some embodiments, the structure for which the model yields the smallest value of $E_{TOTAL}$ is selected as the best structure. However this can lead to convergence at a local minimum rather than a global minimum. In some embodiments, all structures for which the models yield values of $E_{TOTAL}$ below a minimum error threshold are selected as the best structures.

In an illustrated embodiment, each candidate structure Sc is given a probability inversely proportional to the value of $E_{TOTAL}$ for that structure. In these embodiments, a Markov Chain Monte Carlo (MCMC) approach described by Ewens W J, Grant G R *Statistical Methods in Bioinformatics,* 2nd Edn. Springer Verlag: Berlin, 2005 is used to minimize $E_{TOTAL}$. In this approach, a set of candidate models are maintained at each iteration and a particular model survives to the next iteration with probability proportional to the Boltzmann factor exp($E_{TOTAL}$/T), where exp(x)=$e^x$, e is the base of the natural logarithm, and T denotes the "temperature," a measure of the random step size of the search for the most probable condition. As a result, low error models are more likely to be propagated to the next iteration. It is desirable that T is high in the first iterations and low in the later iterations. This approach is often called simulated annealing. The structure selected during step 870 is denoted by $S_{SELECTED}$.

In some embodiments, determining the model constants further comprises randomly selecting a subset of multiple structures based on a probability for each structure inversely related to its minimum error. In these embodiments, the probability $P_c$ associated with each candidate structure $S_c$ is based on the $E_{TOTAL}$ for candidate structure $S_c$, denoted $E_c$, as given by Equation 7.

$$P_c=\exp(-E_c/T)/\{\Sigma_{k=1,C}\exp(-E_k/T)\} \quad (7)$$

$S_{SELECTED}$ is chosen randomly from the $S_c$ based on the $P_c$. Under certain assumptions, the above Markov Chain will have a stationary probability distribution P(t)=A exp(−$E_{TOTAL}$(t)/T), where A is a constant. The assumptions include that the number of neighbors ($l^0$) is the same for every topology represented by $S_c$, c=1 to C; neighbor is a mutual relationship ($w_{ij}$ is non-zero if $w_{ji}$ is non-zero); and all possible topologies can be reached in a finite number of iterations. For a sufficiently small value of T in the later iterations, the algorithm will climb towards a probability optimum or global error minimum.

Control then passes to step 880 to determine if an end condition is satisfied for ending the iteration of structures. Any method may be used to determine whether the end conditions are satisfied. For example, in some embodiments, the end conditions are satisfied if one or more structures have models with associated $E_{TOTAL}$ below a target error threshold. In some embodiments the end condition is that best models on successive iterations of candidate structures have $E_{TOTAL}$ within a certain percentage (e.g., 1%). In some embodiments, the simulation goes on until a large enough statistical sample of possible models is obtained. The generation of multiple models consistent with the data enables one to i) calculate the posterior probability of a particular interaction, given the experimental data; and, ii) in future versions of the method, to computationally identify those hypothetical perturbation experiments that are most likely to be most informative (in the sense that they can be used to "tell apart" possible models). In such embodiments, one gradually reduces the temperature parameter T, following a so-called "cooling schedule".

If it is determined during step 880 that an end condition is satisfied, then control passes to step 790 of method 700 with the best model or models. If not, control passes to step 882 to take as the seed structure $S_{seed}$, the $S_{SELECTED}$ and its associated model constants and $E_{TOTAL}$. Control then passes back to step 810 to generate a new set of candidate structure matrices, and repeat steps 820 through 870.

4. Model of Breast Cancer Cells.

To evaluate the predictive potential of the method, twenty-one drug pair treatment experiments were performed on a human breast cancer cell line (MCF7) while monitoring certain phospho-proteins and cell cycle markers, as an example embodiment. The best derived network model rediscovered known interactions and contained interesting extensions. This model was formed to describe the steady state limit of the response to the perturbations. This example embodiment demonstrates how observations of the effects of drug pair perturbations are exploited to deduce a network model of signaling and phenotype control (reverse engineering of pathways). Observed molecular state and growth phenotype responses were used to build predictive models; and the models were used to explain the perturbation-phenotype relationship in terms of coupling between proteins in the epidermal growth factor receptor (EGFR) to mitogen-activated protein kinase (MAPK) pathway, and lipid kinase phosphoinositol 3 kinase (PI3K) to serine/threonine kinase (AKT, a protein that induces a cancer phenotype in cells) to mammalian target of rapamycin (mTOR) pathway. Without using known pathways to set the non-zero w, the resulting model reproduced known regulatory couplings and negative feedback regulation downstream of EGFR and PI3K/AKT/mTOR, and makes predictions about possible roles of Protein kinase C delta (PKC-δ) and protein synthesis initiation factor 4E (eIF4E) in the control of MAPK signaling and G1 cell cycle arrest in MCF cells, as described in more detail below.

As perturbation agents of the system, we chose compounds {in curly brackets} targeting EGFR {ZD1839, aka Gefitinib}, mTOR {Rapamycin}, multi-enzyme kinase (MEK) {PD0325901, also known as MEKi}, PKC-δ {Rottlerin}, PI3K {LY294002}, and insulin-like growth factor type-1 receptor, IGF1R, {A12 anti-IGF1R inhibitory antibody}. As relevant measurable states of molecular and phenotypic responses we chose phosphoprotein levels of seven regulators of survival, proliferation and protein synthesis: p-AKT-S473; p-ERK-T202/Y204; p-MEK-S217/S221; p-eIF4E-S209; p-c-RAF-S289/S296/S301; p-P70S6K-S371; and p-pS6-S235/S236, also known as p-S6. Also chosen as measureable states were: flow cytometric observation of two phenotypic processes (cell cycle arrest and apoptosis). Inhibitors were administered singly and in pairs, followed by epidermal growth factor (EGF) stimulation. When determining the level of protein phosphorylation in response to the perturbations, we used the average responses at 5 and 30 minutes post perturbation as surrogates for steady state values.

Figure 9A:
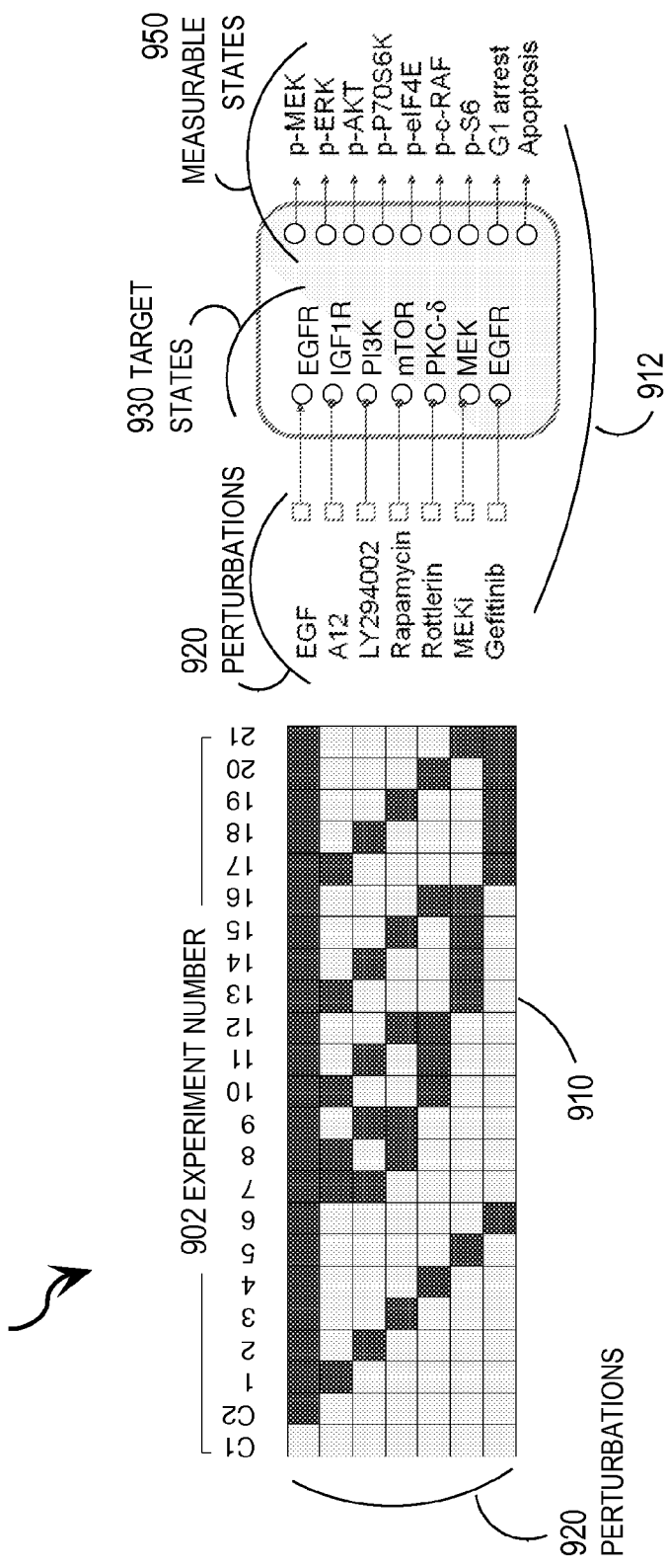
FIG. 9A is a block diagram that illustrates example experiments used to form a network model for breast cancer, according to an embodiment.

FIG. 9A is a block diagram that illustrates example experiments 900 used to form a network model for breast cancer, according to this embodiment. The experiments are represented as a two dimensional block 910 in which the different columns represent experiment number 902 and the different rows represent different perturbations 920. There are 21 experiments used to form the breast cancer network model, and two controls, C1 and C2. The perturbations 920 are listed by name and associated with square input nodes in the network diagram 912, which nodes are aligned with the corresponding row in block 910. There are seven perturbation variables. Each perturbation targets one cell state of target cell states 930 listed by name and represented as circular nodes in the network diagram 912. In this example embodiment, two perturbations target the same cell state variable (EGFR is the target of two perturbations, one at the top and one at the bottom of the list), thus there are six target cell states. The association is indicated by an arrow from a perturbation node 920 to a target cell state node 930. The measureable cell states 950 are listed by name as network model nodes that feed outputs. There are nine measureable cell states, only one of which is a target of the perturbations (e.g., p-MEK is a measurement of MEK, the target for perturbation MEKi, aka PD0325901).

Thus, in the example embodiment, there are six different target cell states and eight unique measurable cell states for a total of N=14 unique cell state variables. The number of measureable cell states in the set Ω is M=9. There is a total of $N^2=196$ possible interaction factors $w_{ij}$ to be determined based on 21 experiments that each provide observed values for all measurable variables for a given set of values for the perturbation variables.

An element of block 910 is filled in if the perturbation corresponding to the row is applied in the experiment indicated by the column of the element. In the illustrated embodiments, the normalized value input as a perturbation when an element of block 910 is filled in is 1.0. In other elements of block 910, no perturbation is applied and the normalized value is zero. The normalized value of perturbations for cell states that are not targets of the perturbation, e.g., the last measurable state, apoptosis, is also zero.

The perturbations 920 for human MCF7 breast tumor cell lines included one natural ligand (EGF) and six inhibitors and were applied during experiments 1 to 21 singly or in combination. The treatment protocol used Epidermal Growth Factor (EGF), an IGF1 receptor inhibitory antibody (A12) and inhibitors of the signaling molecules (target cell states) EGFR, PI3K, mTOR, PKC-6, and MEK. The inhibitors are ZD1839 (Gefitinib), LY294002, Rapamycin, Rottlerin and PD0325901 (MEKi). For each treatment, western blots were used to detect levels of the seven proteins that serve as measurable cell states: phospho-AKT (p-AKT) phospho-ERK (p-ERK), phospho-MEK (p-MEK), phospho-eIF4E (p-eIF4E), phospho-c-RAF (p-c-RAF), phospho-P70S6K (P70S6K), and phospho-pS6 (p-S6). A fluorescent associated cell sorting (FACS) based assay was used to quantify the last two measurable cell states: apoptosis (measured as the 'sub-G1 fraction' as described next) and G1 arrest (measured as the G1 fraction).

MCF-7 cells were obtained from American Type Culture Collection; maintained in 1:1 mixture of DME:F12 media supplemented with 100 units/ml penicillin, 100 µg/ml streptomycin, 4 mM glutamine, and 10% heat-inactivated fetal bovine serum; and incubated at $37_iC$ in 5% CO2. The final concentrations for inhibitors used for perturbation experiments were 1 µM ZD1839 (AstraZeneca), 10 µM LY294002 (Calbiochem), 50 nM PD0325901 (Pfizer), 2 µM Rottlerin (EMD), 10 nM Rapamycin, and 1.5 µg/ml antibody A12 (ImClone Systems).

MCF-7 were grown in 100 mm dishes, and starved for 20 hours in PBS. They were then treated with indicated concentrations of inhibitors or vehicle (DMSO) for 1 hour, followed by adding EGF into the media (final EGF concentration was 100 ng/ml). After EGF stimulation for 5 min or 30 min in the presence of drugs or DMSO, western blots were performed by harvesting MCF-7 cellular lysates in 1% Triton lysis buffer (50 mM HEPES, pH 7.4, 1% Triton X-100, 150 mM NaCl, 1.5 mM $MgCl_2$, 1 mM EGTA, 1 mM EDTA, 100 mM NaF, 10 mM sodium pyrophosphate, 1 mM vanadate, 1× protease cocktail II (Calbiochem) and 10% glycerol), separating 40 µg of each lysate by SDS-PAGE, transferring to PVDF membrance, and immunoblotting using specific primary and secondary antibodies and chemoluminescence visualization on Kodak or HyBlotCL films. Antibodies for phospho-Akt-S473, phospho-ERK-T202/Y204, phospho-MEK-S217/S221, phospho-eIF4E-S209, phospho-c-RAF-S289/S296/S301, phospho-P70S6K-S371 and phospho-pS6-S235/S236 were from Cell Signaling. Films were scanned by a microTEK scanner at 600 dpi in grey scale. Bands were selected and quantified by FUJIFILM Multi Gauge V3.0 software. Each membrane was normalized to internal controls (with or without 100 ng/ml EGF). The membranes were stripped and re-probed with anti-beta actin (Sigma #A5441) to confirm equal protein loading.

For G1 and apoptosis measurements, MCF-7 cells were seeded in 6-well plates (200,000 cells per well) and grown for 20 hours in 10% FBS/DME:F12. Cells were then starved for 20 hours in PBS, and then treated with indicated concentrations of inhibitors or DMSO for 1 hour, followed by adding EGF into the media (final EGF concentration was 100 ng/ml). After EGF stimulation for 24, 48 or 72 hours in the presence of drugs or DMSO, cells were harvested by trypsinization, including both suspended and adherent fractions, and washed in cold PBS. Cell nuclei were prepared by the method of Nusse et al.; and cell cycle distribution was determined by flow cytometric analysis of DNA content (FACS) using red fluorescence of 488 nm excited ethidium bromide-stained nuclei. The percentage of cells in the G1 phase (cell cycle arrest) and sub-G1 fraction (apoptosis) was recorded.

Figure 9B:
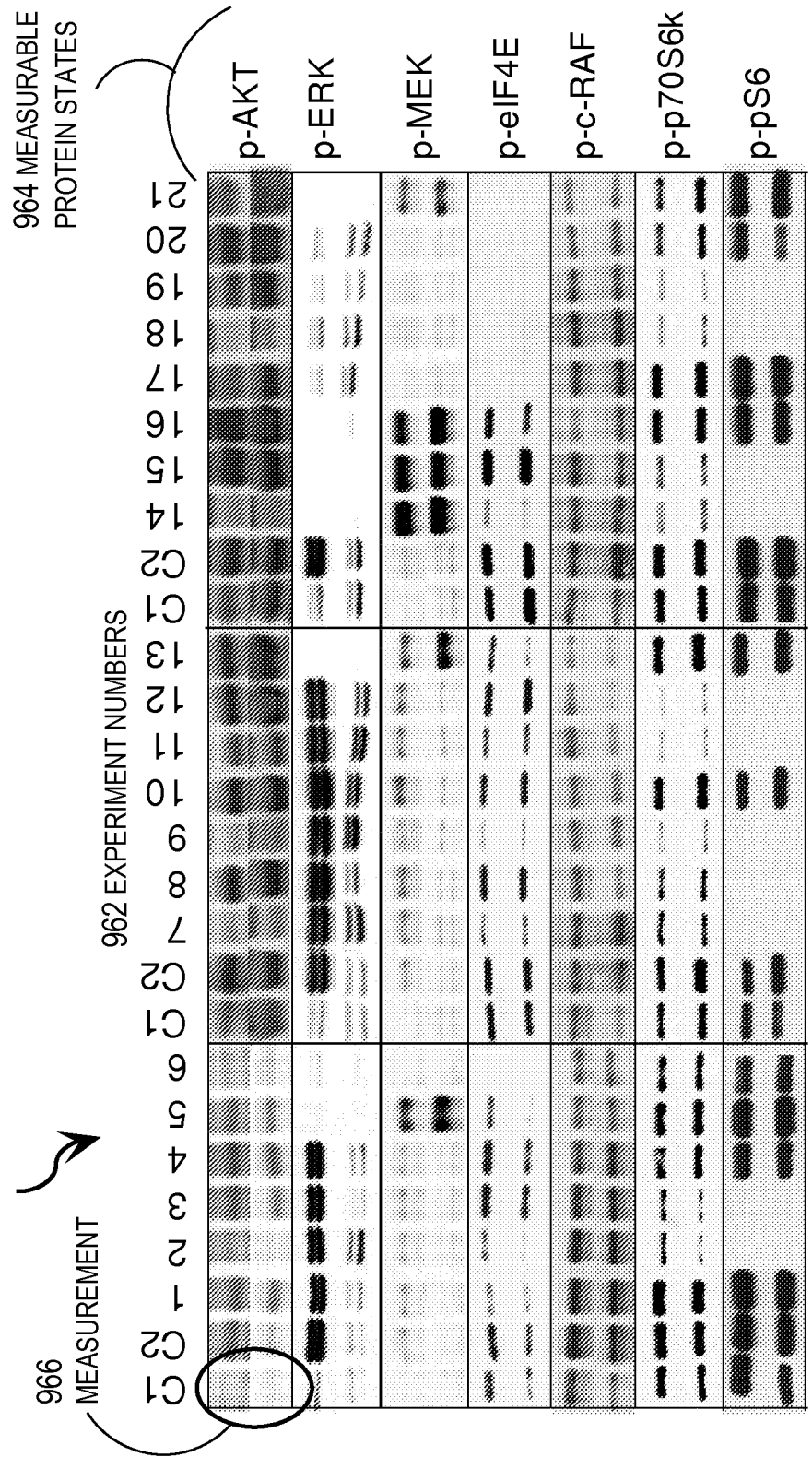
FIG. 9B is a block diagram of example protein measured values for the experiments of FIG. 9A, according to an embodiment.

FIG. 9B is a block diagram of example protein measured values for the experiments of FIG. 9A, according to an embodiment. The measurements 960 are represented as a two dimensional block in which the different columns represent experiment number 962 and the different rows represent different measureable protein states 964 as western blots. The grayscale intensity of this western blot is proportional to the level of protein. An example western blot measurement 966 indicates a level for protein p-AKT during control C1. The measured level of the untreated control (C1) is used as the reference ('wild-type') value $y_0$ in Equation 3a for normalizing the values of the measurable states. Thus the normalized value of the measurement 966 is zero.

Figure 9C:
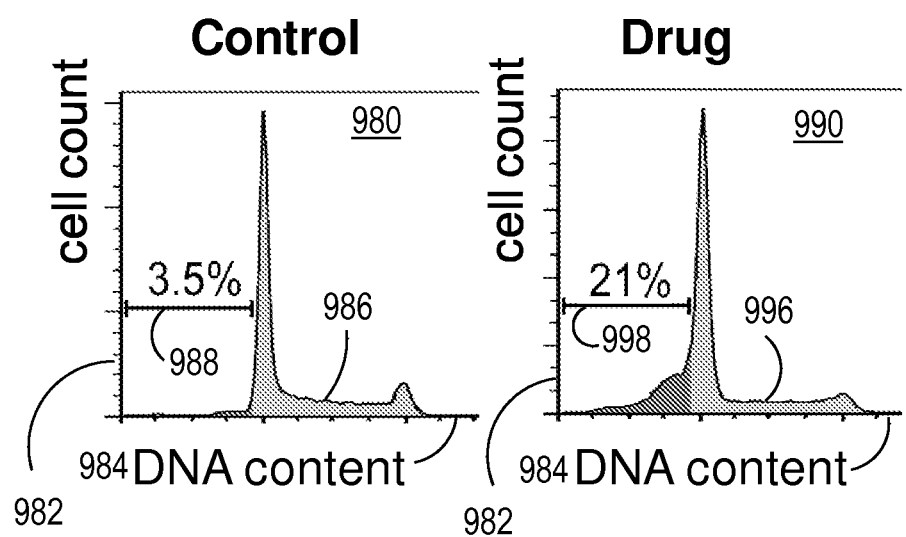
FIG. 9C is a graph of example arrest and apoptosis measured values for an experiment of FIG. 9A, according to an embodiment.

FIG. 9C is a pair of graphs 980 and 990 of example G1 arrest and apoptosis measured values for an experiment of FIG. 9A, according to an embodiment. These graphs present flow histograms depicting cell cycle distribution in MCF-7 cultures treated with perturbant (one experiment) in graph 990 and in untreated controls (control C1) in graph 980. The horizontal axis 984 is DNA content of the culture and the vertical axis 954 is cell count, in both graphs 980 and 990. Curve 986 shows the distribution of cell count with DNA content for the control and Curve 996 shows the distribution of cell count with DNA content in response to the perturbant. The percentage of cells in the G1 phase (cell cycle arrest) is indicated by a curve fit to the peak in each of curve 986 and curve 996, as is well known in the art. Apoptosis (programmed cell death) is indicated by the fraction of the total cell count with DNA content less than the peak, which fraction is called the sub-G1 fraction. As can be seen, in the control only 3.5% of the cells underwent apoptosis; while about 21% of the perturbant treated cells underwent apoptosis. Thus the percentage in G1 arrest and apoptosis in graph 980 are the y0 "wild" values used during normalization of G1 arrest and apoptosis, respectively, in Equation 3a.

To build models in this embodiment, each of the above unique perturbation targets (signaling proteins), as well as each of the unique observable properties, is represented by one state variable $y_i$, i=1, 14.

Figures 10A, 10B:
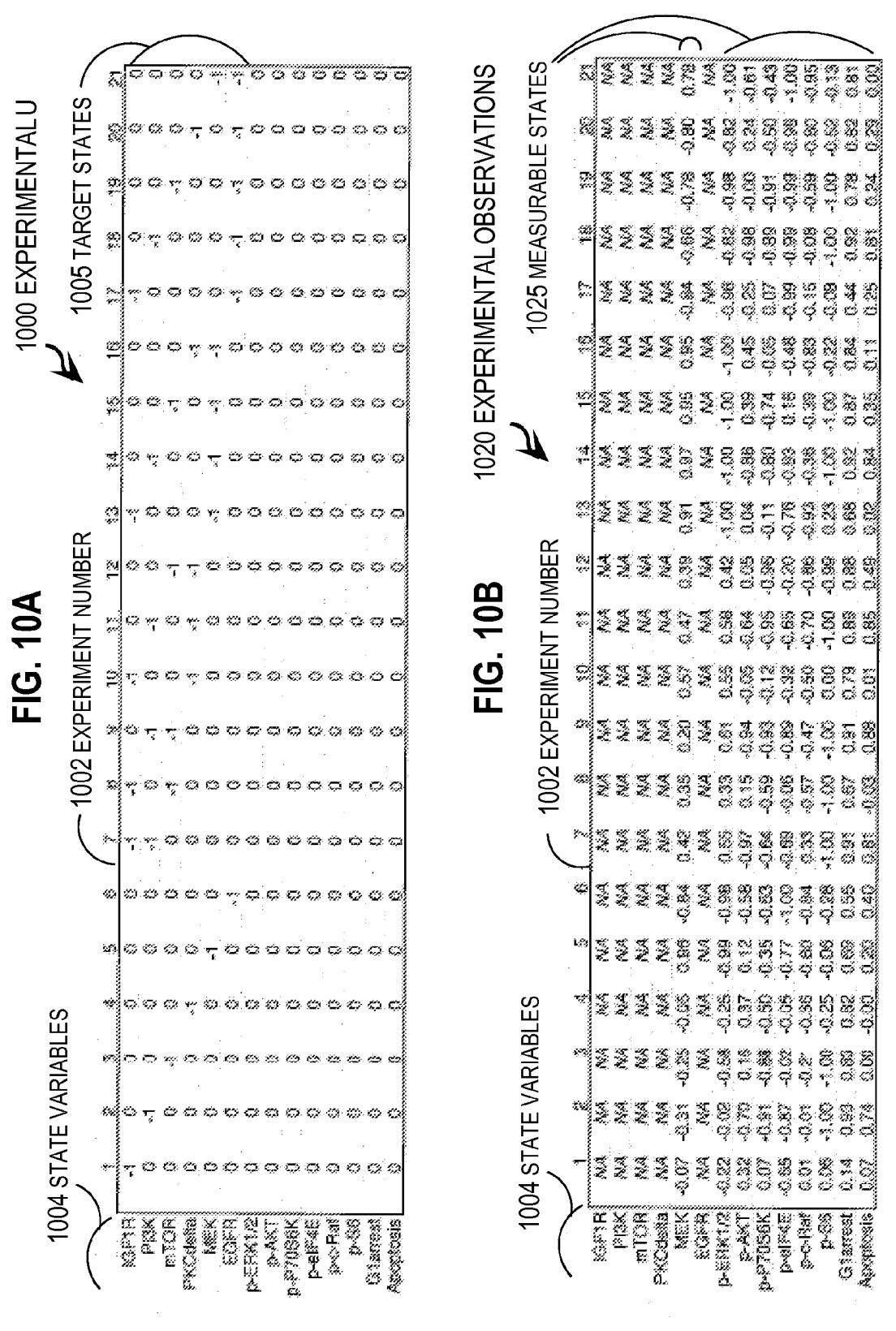

FIG. 10A is a block diagram that illustrates an example vector of perturbation values u 1000 for each of the 21 experiments, according to an embodiment. The experimental perturbations u 1000 are represented as a two dimensional array in which the different columns represent experiment number 1002 and the different rows represent different state variables y 1004. As stated above there are 14 unique state variables y 1004. The perturbation values 1000 are listed in the rows of the target state variables 1005, which are a subset of all the state variables y 1004. As stated above, there are seven perturbation variables but only six target state variables 1005. Thus the perturbation values for the state variables that are not targets of the perturbations are zero for all experiments. The perturbation values for the state variables that are target states 1005 are shown as zero in experiments where the perturbations are not applied and −1 to indicate an inhibitory perturbation in experiments where the perturbations are applied.

FIG. 10B is a block diagram that illustrates an example vector of observed values 1020 for the cell state variables for each of 21 experiments, according to an embodiment. The experimental observations Ω 1020 are represented as a two dimensional array in which the different columns represent experiment number 1002 and the different rows represent different state variables y 1004, as in FIG. 10A. The experimental values Ω 1020 are listed in the rows of the measurable state variables 1025, which are a subset of all the state variables y 1004. As stated above, there are nine measurable state variables 1025. Thus the observed values for the state variables y that are not measurable state variables Ω are designated "not applicable (NA)" for all experiments. The observed values for the state variables that are measurable state variables Ω 1025 are shown as normalized values determined using Equation 3a, and thus fall in the range from about −1.00 to about +1.00 (e.g., from about half to about twice the value in the control). In some embodiments, values outside the range −1.0 to +1.0 are replaced by the nearest value in the range. In some embodiments, measurements are standardized by division with the sample variance, so that all measurements for a particular variable have variance=1. In some other embodiments, the signal is transformed by a continuous function y=f(x), for which input values are any real number, and for which output values y are real numbers on the interval −1<y<1.

The methods of FIG. 8 are then used to estimate the interaction factors $w_{ij}$ and other constants of the model, resulting in one or more good predictive models of response in terms of these system variables. In the example embodiment, the following choices were made. Step 802 was omitted and no interaction factors were considered known or accepted a priori. In step 804 the initial seed structure was determined to have no non-zero interaction factors, i.e., $S_{ij}=0$ for all i and j. In step 810 a set of candidate structures was generated by adding one edge (i.e., one non-zero element $S_{ij}=1$) to the seed structure. Thus, for the first iteration there are 196 candidate structure matrices Sc, each with one non-zero value at a different (row, column) location. In step 820 the non-zero values of w were initialized to 1.0; and the initial values for α and β were set equal to 1.0 for all i=1,14.

In steps 830 to 880, Equations 5a through 5e were employed with $\phi_i(x)=\phi(x)=\tan h(2x)$ for all i=1, 14. In addition η was set equal to 0.00001, μ=1.5 and T=1. Using the Monte Carlo algorithm for 450 iterations, a population of 450 good models were generated from the 21 MCF7 dual drug perturbation experiments.

The resulting model constants of the best model (smallest total error) of the 450 good models give equations for $dy_i/dt$ based on Equation 2 for the 14 state variables as presented in Equations 8a through 8n:

$$d\text{IGFIR}/dt=\phi(-\text{A12})-\text{IGFIR} \quad (8a)$$

$$d\text{P13K}/dt=1.14\phi(0.05\text{p-eIF4E}-\text{LY2940022})-0.84\text{P13K} \quad (8b)$$

$$d\text{mTOR}/dt=1.04\phi(-\text{Rapamycin})-0.96\text{mTOR} \quad (8c)$$

$$d\text{PKCdelta}/dt=1.05\phi(-\text{Rottlerin})-0.95\text{PKCdelta} \quad (8d)$$

$$d\text{MEK}/dt=0.63\phi(-0.21\text{MEK}+0.76\text{EGFR-PD901})-1.27\text{MEK} \quad (8e)$$

$$d\text{EGFR}/dt=1.25\phi(-0.34\text{p-ERK1/2}+0.37\text{G1arrest-EGF})-0.66\text{EGFR} \quad (8f)$$

$$d\text{p-ERK1/2}/dt=1.13\phi(0.41\text{MEK}+0.32\text{p-ERK1/2}-0.13\text{G1arrest})-0.86\text{p-ERK1/2} \quad (8g)$$

$$d\text{p-AKT}/dt=\phi(0.55\text{P13K})-\text{p-AKT} \quad (8h)$$

$$d\text{p-P70S6K}/dt=1.12\phi(0.28\text{mTOR}-0.41\text{Apoptosis})-0.87\text{p-P70S6K} \quad (8i)$$

$$d\text{p-eIF4E}/dt=1.07\phi(0.21\text{p-ERK1/2}-0.33\text{G1arrest})-0.92\text{p-eIF4E} \quad (8j)$$

$$d\text{p-c-RAF}/dt=1.08\phi(0.29\text{PKCdelta}+0.3\text{MEK}-0.07\text{EGFR})-0.91\text{p-c-RAF} \quad (8k)$$

$$d\text{p-S6}/dt=1.13\phi(0.52\text{p-P70S6K})-0.85\text{p-S6} \quad (8l)$$

$d\text{G1arrest}/dt = 1.11\phi(-0.05\text{IGFIR} - 0.14\text{PKCdelta} - 0.24\text{p-eIF4E} + 0.4\text{Apoptosis}) - 0.87\text{G1arrest}$ (8m)

$d\text{Apoptosis}/dt = 1.09\phi(-0.06\text{mTOR} - 0.42\text{p-AKT}) - 0.91\text{Apoptosis}$ (8n)

When this system is propagated through time, it will generally converge to a stable, fixed point. We interpret this fixed point as the steady state phenotypic response to the perturbation u. To calculate the fixed point given a model, we start in the wild state and used standard numerical integration methods (see for example, ode15s from Mathworks, Inc. and DLSODE).

The predictive power of the derived models was assessed using leave-one-out cross-validation, in which one experiment (a paired set of values for u and Ω) is left out of the model derivation and then its observed values predicted using model constants gleaned from the remaining experiments. The resulting predictions were reasonably accurate for the nine different measurable state variables Ω.

FIG. 11A and FIG. 11B are block diagram comparing example model output 1150 and example measured values 1100, according to an embodiment. The results are represented as a two dimensional array of squares in which the different columns represent experiment number 1102 and the different rows represent different measurable states 1104. Results are presented for 21 experiments used to form the breast cancer network model. The measurable state variables 1104 are listed by name. A scale 1110 indicates the value associated with each result. The darker square has the larger value and positive values 1114 are hatched and negative values 1112 are solid. The range is from about −1.0 to about +1.0. The top array indicates the observed values 1100 in the 21 experiments. The bottom array indicates the predicted values 1150 generated by the model using the model constants derived from 20 of the 21 experiments, leaving out the data being predicted, and the corresponding values for the perturbation variables for each experiment.

FIG. 11 shows good agreement between experimental observation (top) of the response of the MCF7 cell line to the 21 different perturbations and the model prediction (bottom). Recall that for each result, the system's response is quantified by the phenotypic index defined as the log relative response in treated versus untreated cells (Equation 3a). For some drug combinations, the phenotypic readout increases as a result of perturbation (hatched), for others it decreases (solid).

The statistics of prediction performance were accumulated for both the non-linear model based on Equation 2 and more traditional linear transfer functions; and are presented in Table 1A and Table 1B. Table 1A shows the cross validation error (CV) as the mean-squared prediction error for predicting a particular measurable state variable. Considering just the performance of the non-linear models, the best prediction was obtained for p-S6 phosho-protein levels (cross-validation error CV=0.02, Pearson correlation r=0.96) and the weakest for the G1 arrest phenotype (CV=0.07, r=0.45).

TABLE 1A

Cross-validation error.

| Measurable State | Linear model | Non-linear model | % error reduction using non-linear model (p = 0.027) |
|---|---|---|---|
| MEK | 0.58 | 0.25 | 57 |
| p-ERK1/2 | 0.30 | 0.09 | 71 |
| p-AKT | 0.10 | 0.06 | 39 |
| p-P70S6K | 0.05 | 0.03 | 25 |
| p-eIF4E | 0.09 | 0.09 | 3 |
| p-c-RAF | 0.11 | 0.11 | 4 |
| p-S6 | 0.06 | 0.02 | 73 |
| G1arrest | 0.07 | 0.07 | −10 |
| Apoptosis | 0.04 | 0.03 | 12 |

TABLE 1B

Pierson correlation between predicted and observational values.

| Measurable State | Linear model | Non-linear model | Correlation increase (p = 0.020) |
|---|---|---|---|
| MEK | −.014 | 0.64 | 0.77 |
| p-ERK1/2 | 0.63 | 0.92 | 0.29 |
| p-AKT | 0.82 | 0.89 | 0.07 |
| p-P70S6K | 0.79 | 0.91 | 0.12 |
| p-eIF4E | 0.67 | 0.69 | 0.02 |
| p-c-RAF | 0.53 | 0.64 | 0.11 |
| p-S6 | 0.82 | 0.96 | 0.14 |
| G1arrest | 0.49 | 0.45 | −0.04 |
| Apoptosis | 0.85 | 0.88 | 0.03 |

The performance of the non-linear network modeling approach is compared directly to one using a corresponding set of linear differential equations with the same optimization procedure. By comparison, predictions using the non-linear approach agreed better with experimental observations for 8 of the 9 measurable state variables. Using the non-linear modeling approach, the prediction error was lower by up to 50% with correspondingly better correlation between predictions and experimental observations. The comparison is significant at the levels indicated by p in each table using the paired Wilcoxon ranked test to test the hypothesis that the difference between the paired samples comes from a distribution whose median value is zero. Thus, it is concluded that the model formation method of FIG. 7 and FIG. 8 is capable of deriving reasonably accurate network models for the input-output behavior of MCF7 cells with respect to the measurable state variables used.

Figure 12:
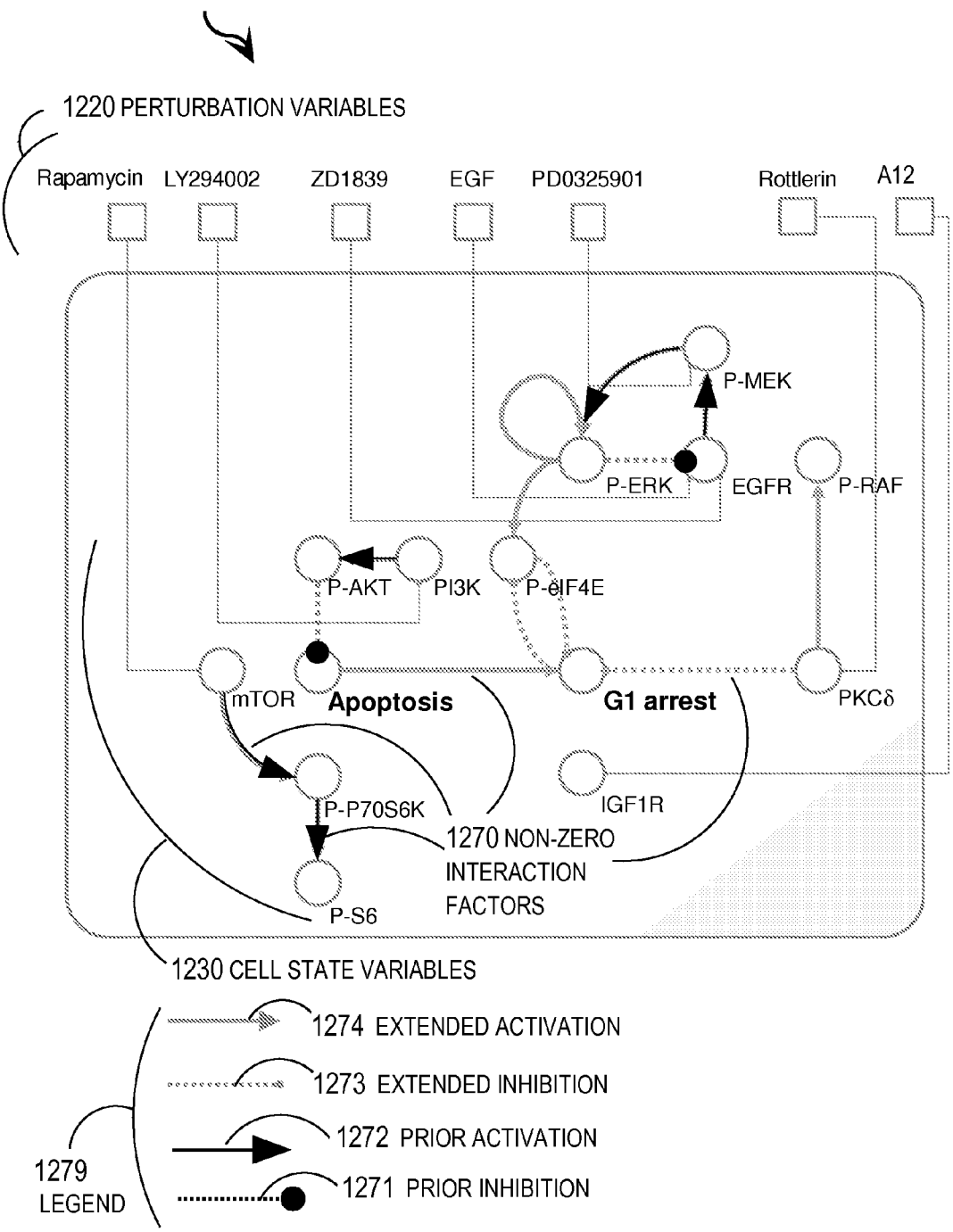
FIG. 12 is a block diagram that illustrates an example network model for treatment of breast cancer, according to an embodiment.

FIG. 12 is a block diagram that illustrates an example network model 1200 for treatment of breast cancer, according to an embodiment. This model shows in diagram form the sign and direction of the non-zero interaction factors $w_{ij}$. The seven perturbation variables 1220 are represented as square input nodes. The fourteen cell state variables 1230 are represented as circular nodes. The non-zero interaction factors $w_{ij}$ 1270 are represented as arrows with triangular arrowheads for activation (positive) interaction factors and circular arrowheads for inhibition (negative) interaction factors, as indicated in legend 1279. The existence of some of these non-zero interaction factors are previously known or accepted as indicated by the large arrowheads 1271 for prior inhibition and 1272 for prior activation in legend 1279. However, the existence of some of these non-zero interaction factors are not previously known or accepted, and thus the pathways are extended by virtue of the model formation process, as indicated by the small arrowheads 1273 for extended inhibition and 1274 for extended activation in legend 1279.

From the set of perturbation experiments, the logical network structure of activating and inhibiting interactions between the key molecular components, similar to the familiar pathway diagrams in publications summarizing a set of molecular biological experiments, are deduced. Here, the derived network models with the smallest total error ($E_{TOTAL}=E_{SSQ}+\lambda E_{STRUCT}$) is used to infer causal connectivity diagrams. The inference is based on the assumption that interactions in sufficiently simple models that fit experimental observations, called 'good' models, represent an underlying causal relationship between system components modeled by the system variables $y_i$. Such a relationship can be either an indirect regulatory effect or a direct physical interaction that would be observable in vitro with purified components.

The interaction matrix $w_{ij}$ from a set of good models can be used to infer regulatory interactions as shown in FIG. 12. Positive $w_{ij}$ means activation, negative $w_{ij}$ means inhibition of the destination state. Interestingly, some of the interactions are well known in MCF7 cells (large arrowheads) and others constitute extensions (small arrowheads). No underlying accepted pathway model was used—the network is a straightforward interpretation of the optimized model parameters $w_{ij}$. The EGFR→MEK→ERK and PI3K→AKT, canonical pathways are identified. Also, note that the extended interactions detect self-inhibitory interactions in MEK/ERK signaling, and identification of eIF4E and AKT as direct regulators of Apoptosis and G1 arrest.

From the 450 good models, the statistical significance of the individual interactions were assessed both in terms of a posterior probability (which is obtained directly from the Monte Carlo process) and a 90% confidence interval constructed by boot-strapping simulations.

For a given model structure S, re-sampling of residuals was used to generate boot-strapped confidence intervals for the model parameters. First, the model was fitted using structure S and the original data, and residuals calculated as the best model fit minus the original data. A total of 200 'new' data-sets were then constructed by adding randomly drawn residuals to each measurement (using residuals for the corresponding measurable variable, e.g., p-MEK residuals were added to p-MEK values and so on). For each such re-sampled data-set, a model was fitted using the structure S. Subsequently, confidence intervals for each interaction factor were calculated as percentiles 5%-95% across the 200 data-sets.

The connectivity of the best model, i.e., the one with the smallest total error, is depicted in FIG. 12 and discussed relative to the known biology of regulatory pathways in the MCF7 breast cancer cell line. The inferred connectivity is compared with mechanisms known to occur in MCF7 cells in Table 2.

TABLE 2

Statistical assessment of inferred interactions in MCF7 cells. Bold interactions are prior known, the remaining interactions are extensions identified herein.

| Regulator (Source) | Target (Destination) | Mean | 90% CI | | Posterior Probability (%) | |
|---|---|---|---|---|---|---|
| EGFR | MEK | 0.78 | 0.67 | 0.88 | 99 | 0 |
| MEK | p-ERK | 0.39 | 0.26 | 0.48 | 99 | 0 |
| PI3K | p-AKT | 0.57 | 0.47 | 0.69 | 93 | 0 |
| PKCdelta | p-c-RAF | 0.25 | 0.17 | 0.32 | 71 | 0 |
| mTOR | p-S6 | 0.25 | 0.20 | 0.29 | 41 | 0 |
| p-ERK | p-eIF4E | 0.19 | 0.14 | 0.25 | 38 | 0 |
| p-ERK | p-ERK | 0.29 | 0.22 | 0.40 | 35 | 0 |
| p-70S6K | p-S6 | 0.54 | 0.53 | 0.56 | 20 | 0 |
| Apoptosis | G1arrest | 0.37 | 0.30 | 0.44 | 20 | 0 |
| G1arrest | EGFR | 0.39 | 0.29 | 0.49 | 13 | 0 |
| MEK | p-c-RAF | 0.29 | 0.16 | 0.41 | 13 | 0 |
| p-eIF4E | PI3K | 0.05 | 0.02 | 0.08 | 13 | 1 |
| p-AKT | Apoptosis | −0.39 | −0.43 | −0.36 | 0 | 77 |
| PKCdelta | G1arrest | −0.12 | −0.20 | −0.06 | 0 | 41 |
| p-ERK | EGFR | −0.28 | −0.42 | −0.17 | 0 | 36 |

TABLE 2-continued

Statistical assessment of inferred interactions in MCF7 cells. Bold interactions are prior known, the remaining interactions are extensions identified herein.

| Regulator (Source) | Target (Destination) | Mean | 90% CI | | Posterior Probability (%) | |
|---|---|---|---|---|---|---|
| G1arrest | p-eIF4E | −0.33 | −0.36 | −0.30 | 0 | 32 |
| p-eIF4E | G1arrest | −0.19 | −0.25 | −0.12 | 0 | 20 |
| Apoptosis | p-S6 | −0.39 | −0.42 | −0.36 | 0 | 19 |
| IGF1R | G1arrest | −0.06 | −0.14 | 0.01 | 0 | 16 |
| G1arrest | p-ERK | −0.09 | −0.16 | −0.01 | 1 | 15 |
| mTOR | Apoptosis | −0.07 | −0.12 | −0.02 | 1 | 12 |
| MEK | MEK | −0.13 | −0.21 | −0.07 | 0 | 8 |
| EGFR | p-c-RAF | −0.03 | −0.11 | 0.04 | 6 | 2 |

In Table 2, the column labeled "mean" indicates the average interaction strength between the target and the regulator, as obtained from 200 bootstrapping simulations. 90% confidence intervals for the interaction strength are shown in the next columns. The left column of the posterior probabilities shows the fraction of models with a positive regulation in the Monte Carlo simulation. The right column under this heading shows the fraction of models with negative regulation (e.g., inhibition of apoptosis by p-AKT was present in 77% of models).

Two caveats are important. (1) The logical nodes in the example models are defined precisely as the perturbed and observed molecular species, i.e., the targets of drug perturbation and the targets of specific observed antibody reactions, and may not be exactly identical to a single molecular species. For example, "EGFR" refers to the direct target(s) of activation by EGF and of inhibition by the drug ZD1839, and these two are assumed to be identical. (2) The models make no reference to unperturbed or unobserved nodes, e.g., while p-AKT is in the network model, the unphosphorylated AKT is not. With these caveats in mind, one can use the models both for confirmation and prediction of interactions.

Of the 23 interactions in the best model, 14 had a posterior probability in the range 20% to 99%. Of these, several statistically robust interactions clearly confirm canonical pathway structures. (i) The MAPK cascade downstream of the EGF receptor is detected as a chain of interactions between EGFR, MEK and ERK. (ii) The negative feedback regulation of MAPK signaling is captured as negative interaction from ERK to EGFR, and as a moderately significant self-inhibition of MEK. (iii) PI3K dependent signaling and the tendency for MCF7 cells to be dependent on AKT activation for survival are detected as interactions between PI3K, AKT and the apoptosis phenotype. (iv) The model inference that apoptosis is controlled by pAKT, but not pERK, is in agreement with previous results in MCF7 cells. (v) mTOR downstream signaling is detected as interactions between mTOR, P70S6K and ribosomal S6 protein. The derivation of these expected interactions from a small set of perturbation experiments, without prior pathway knowledge, underscores the non-trivial value of the model building approach and provides some confidence in the concrete predictions of logical regulatory interactions for MCF7 cells as listed in Table 2.

In summary, these evaluations in breast cancer cells support two main conclusions. First, the method 800 for determining model constants can be used to build reasonably accurate quantitative predictors of pathway responses to combinatorial drug perturbation in MCF7 cells. Second, the quality of the deduced interaction network suggests that well-parameterized non-linear MIMO models are interpretable in terms of a network of (direct and/or indirect) regulatory interactions. The inference of network structure is surprisingly effective: the logical network diagram in FIG. 12 was derived de novo based on only 21 experiments, using non-temporal data and only nine measurable state variables; yet accurately reflects important known regulatory interactions. This bodes well for future applications in which the number of measurable variables and experiments to populate them can easily be an order of magnitude greater. In addition to yielding details of intermolecular coupling, the method is sufficiently general to allow predictive modeling of causal relationships between biomolecular events and cellular phenotypic consequences, such as growth or cell cycle arrest. The method lends itself to multi-level modeling in the sense that molecular, mesoscopic and macroscopic events can be modeled in a single framework once appropriate state variables $y_i$ are defined.

The non-linear representation proposed here, or related neural models, have been used in biological contexts such as transcriptional network modeling, in synthetic biology and for problems such as approximation of chemical reactions. In addition, the non-linear models developed herein are similar, but not identical, to Hopfield networks, a formalism introduced to study computation in physical systems. This bodes well for modeling reactions involved in DNA and RNA switches.

In a recent interesting work, Lehar et al., 2007 used drug pairs to perturb signaling pathways in cancer cells, and provided an interpretation framework based on traditional pharmacological models for two-drug response surfaces. Drug targets in the PI3K and MAPK pathways were characterized by correlating 'synergy profiles', demonstrating a link between network connectivity and drug pair response. Such synergy profiles, in turn, can be thought of as a generalization of the epistasis matrix used by Segre et al. 2005 as a basis for functional clustering of genes. The approach proposed here is different in the sense that it performs a global optimization that aims to find a fully parameterized model for the entire system. Such models, in turn, can be used for additional purposes such as making predictions of system responses, or making connectivity information explicit as pathway diagrams. Preliminary data suggest that non-linear models as determined herein can be used to interpret or predict response surface data, as a function of drug concentrations, which would integrate our method with the approach of Lehar et al., 2007, e.g., to reduce experimental cost. Finally, the differential equation in Equation 2 can easily be represented in standard systems biology formats, such as BioModels and be used with a number of tools for model visualization, numerical simulation or analytical characterization. Thus the tools described herein can be made readily available to other workers in the field.

In the analysis of the model depicted in FIG. 12, self-inhibitory feedback loops were detected downstream of the EGF receptor. This is compatible with the observation that receptor activation of MAPK signaling frequently leads to rapid feedback inhibition, for instance by induced expression of inhibitory proteins (such as Sprouty or MAPK phosphatases), or inhibition of RAF by direct phosphorylation.

The illustrated example does not identify the full complexity of the feedback loops, because nodes such as ERK or RAF-1 or other proteins were not perturbed; and a short EGF stimulation time was used. Additional predictions, such as (i) eIF4E acting as a downstream effector of ERK, as well as (ii) PKCdelta counteracting the G1 arrest phenotype, are supported by results in other cell types. Furthermore, the model predicts a mutually inhibitory interplay between eIF4E activation by phosphorylation and G1 arrest, consistent with the established role of eIF4E as a potent oncogene and a master activator of a 'regulon' of cell cycle activator genes. However, the extended pathway that increases p-RAF by PKCdelta is paradoxical: the observed phosphorylation sites on p-c-RAF (S289/S296/S301) are regarded as inhibitory, which seems inconsistent with the fact that PKCdelta can activate MAPK signaling in a RAF-dependent way. This extension might suggest an unknown direct effect mechanism, or an indirect effect that is not captured in the present analysis. Finally, three less interpretable and therefore interesting or potentially problematic, features of the network in FIG. 12 are (i) the self-activation of ERK; (ii) the activating arrow between apoptosis and G1 arrest; and, (iii) the fact that RAF is not placed between EGFR and MEK, as in the usual representation of this pathway. Overall, a number of the predictions can be used to design experiments to validate or refute the model predictions.

It is concluded that non-linear modeling of cell states may be of interest as a broadly applicable tool to construct models, discover regulatory and molecular interactions, and predict cellular and biological system responses. For instance, researchers can measure a set of protein phosphorylation responses to drug combinations and use the method to automatically construct network models that predict the response to novel drug combinations. Application of this methodology to time-dependent experimental observations would extend this predictive capability to the regime of time-dependent, rationally designed combinatorial therapy. It is further suggested to use of such models to optimize therapeutic protocols, especially by designing interventions using a combination of targeted compounds administered in an optimal time sequence. The methods presented here constitute a concrete step towards the active development of network-oriented pharmacology.

For example, a set of one or more drugs are selected based on efficacy determined by running a model for the biological system targeted by the drugs. As used here the term drug refers to a chemical compound or composition capable of inducing a desired therapeutic effect when properly administered to a patient. The term "drug" includes "bioactive agents." "Bioactive agents" as used herein includes any molecule, e.g., protein, oligopeptide, small organic molecule, polysaccharide, polynucleotide, lipid, etc., or biologically active fragment or variant thereof, including mixtures thereof, with the capability of directly or indirectly altering the bioactivity of one of the various proteins.

Figures 13A, 13B:
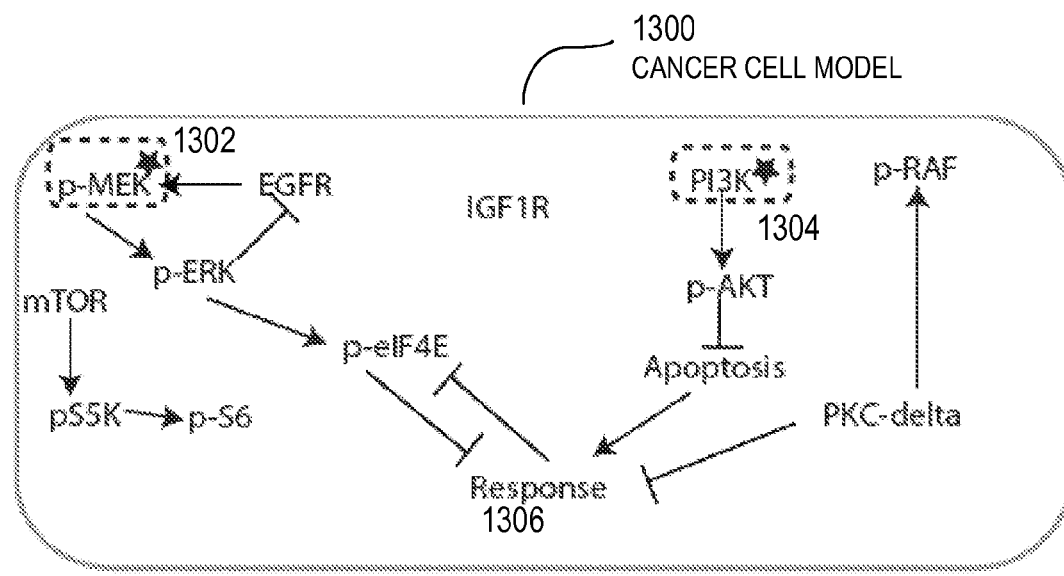
FIG. 13A is a diagram that illustrates a cell model for a breast cancer cell, according to an embodiment.
FIG. 13B is a diagram that illustrates a series of model runs predicting cell response to different drugs and drug pairs, according to an embodiment.

FIG. 13A is a diagram that illustrates a cell model 1300 for a breast cancer cell, according to an embodiment. This model 1300 is similar to the model 1200 described in FIG. 12, but allows for more perturbation variables (not shown). State variable 1302 representing MEK level and state variable 1304 representing PI3K levels are each indicated by a star. The Response 1306 corresponds to G1 arrest. Activating interactions are represented by triangular arrowheads and inhibiting interactions by flat arrowheads.

FIG. 13B is a diagram 1310 that illustrates a series of model runs predicting cell response to different drugs and drug pairs, according to an embodiment. Each of 13 drugs potentially administered as perturbation agents are represented by a row 1312. Each of 91 model runs is represented by a column 1314. In each model run, the drug administered as a perturbation agent (non-zero perturbation variable) is indicated by a solid filled box. As shown in diagram 1310, in each of the 91 model runs, the response is computed for a different drug or pair of drugs.

Figure 13C:
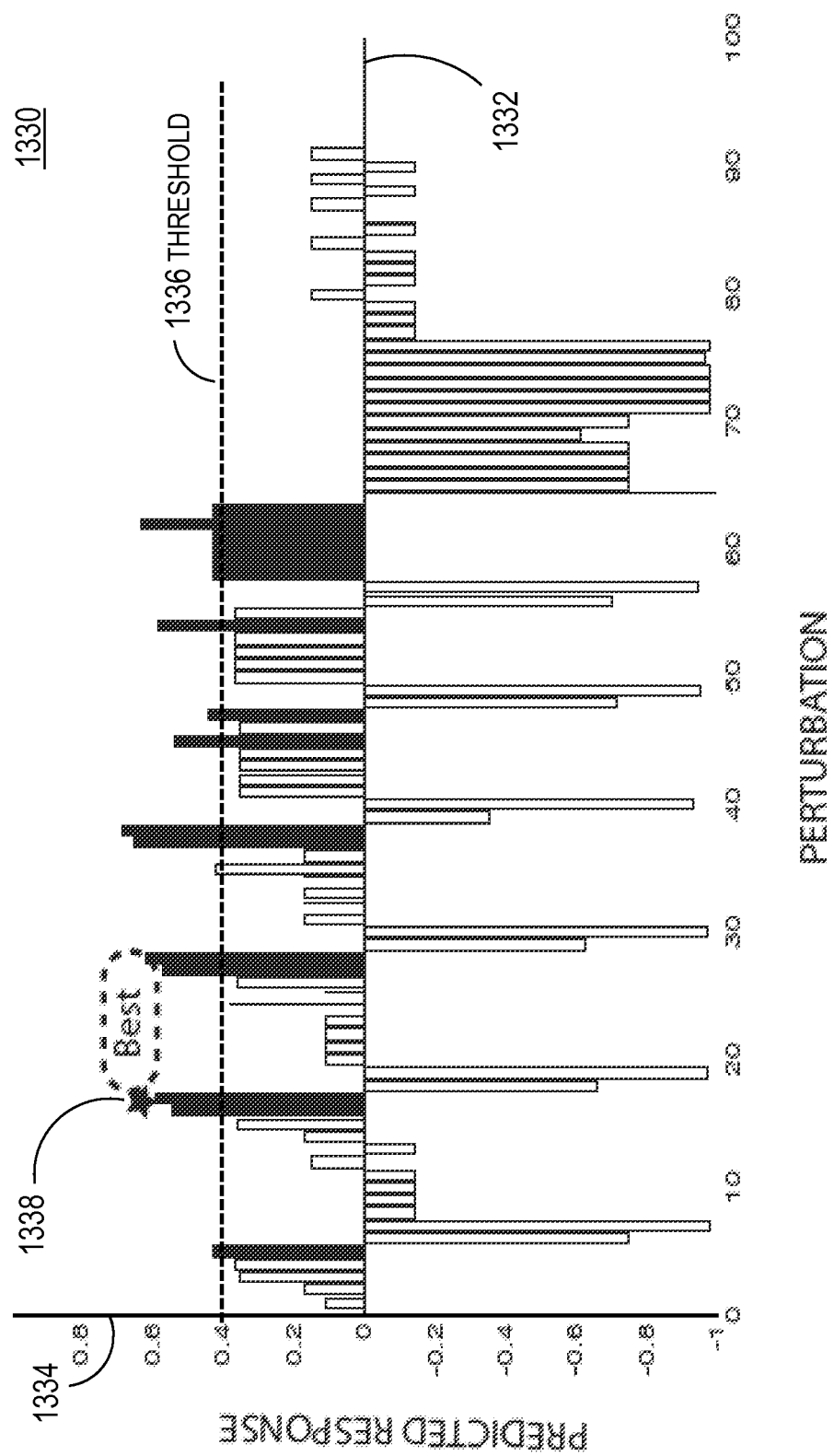
FIG. 13C is a bar graph that illustrates a predicted response for each model run, according to an embodiment.

FIG. 13C is a bar graph 1330 that illustrates a predicted response for each model run, according to an embodiment. The horizontal axis 1332 indicates model run in the order depicted in FIG. 13B. The vertical axis 1334 indicates computed G1 arrest response in percent. Desirable responses exceed the threshold percentage 1336. Of these, the best response is indicated by a star, which corresponds to model run 18, which is a combination of a first drug and a sixth drug. This combination involves a MEK inhibitor and a P13K inhibitor. According to the model 1300, this combination is most likely to be an effective drug combination.

5. Hardware Overview

FIG. 14 is a block diagram that illustrates a computer system 1400 upon which an embodiment of the invention may be implemented. Computer system 1400 includes a communication mechanism such as a bus 1410 for passing information between other internal and external components of the computer system 1400. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). A sequence of binary digits constitutes digital data that is used to represent a number or code for a character. A bus 1410 includes many parallel conductors of information so that information is transferred quickly among devices coupled to the bus 1410. One or more processors 1402 for processing information are coupled with the bus 1410. A processor 1402 performs a set of operations on information. The set of operations include bringing information in from the bus 1410 and placing information on the bus 1410. The set of operations also typically include comparing two or more units of information, shifting positions of units of information, and combining two or more units of information, such as by addition or multiplication. A sequence of operations to be executed by the processor 1402 constitute computer instructions.

Computer system 1400 also includes a memory 1404 coupled to bus 1410. The memory 1404, such as a random access memory (RAM) or other dynamic storage device, stores information including computer instructions. Dynamic memory allows information stored therein to be changed by the computer system 1400. RAM allows a unit of information stored at a location called a memory address to be stored and retrieved independently of information at neighboring addresses. The memory 1404 is also used by the processor 1402 to store temporary values during execution of computer instructions. The computer system 1400 also includes a read only memory (ROM) 1406 or other static storage device coupled to the bus 1410 for storing static information, including instructions, that is not changed by the computer system 1400. Also coupled to bus 1410 is a non-volatile (persistent) storage device 1408, such as a magnetic disk or optical disk, for storing information, including instructions, that persists even when the computer system 1400 is turned off or otherwise loses power.

Information, including instructions, is provided to the bus 1410 for use by the processor from an external input device 1412, such as a keyboard containing alphanumeric keys operated by a human user, or a sensor. A sensor detects conditions in its vicinity and transforms those detections into signals compatible with the signals used to represent information in computer system 1400. Other external devices coupled to bus 1410, used primarily for interacting with humans, include a display device 1414, such as a cathode ray tube (CRT) or a liquid crystal display (LCD), for presenting images, and a pointing device 1416, such as a mouse or a trackball or cursor direction keys, for controlling a position of a small cursor image presented on the display 1414 and issuing commands associated with graphical elements presented on the display 1414.

In the illustrated embodiment, special purpose hardware, such as an application specific integrated circuit (IC) 1420, is coupled to bus 1410. The special purpose hardware is configured to perform operations not performed by processor 1402 quickly enough for special purposes. Examples of application specific ICs include graphics accelerator cards for generating images for display 1414, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1400 also includes one or more instances of a communications interface 1470 coupled to bus 1410. Communication interface 1470 provides a two-way communication coupling to a variety of external devices that operate with their own processors, such as printers, scanners and external disks. In general the coupling is with a network link 1478 that is connected to a local network 1480 to which a variety of external devices with their own processors are connected. For example, communication interface 1470 may be a parallel port or a serial port or a universal serial bus (USB) port on a personal computer. In some embodiments, communications interface 1470 is an integrated services digital network (ISDN) card or a digital subscriber line (DSL) card or a telephone modem that provides an information communication connection to a corresponding type of telephone line. In some embodiments, a communication interface 1470 is a cable modem that converts signals on bus 1410 into signals for a communication connection over a coaxial cable or into optical signals for a communication connection over a fiber optic cable. As another example, communications interface 1470 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1470 sends and receives electrical, acoustic or electromagnetic signals, including infrared and optical signals, that carry information streams, such as digital data.

The term computer-readable medium is used herein to refer to any medium that participates in providing information to processor 1402, including instructions for execution. Such a medium may take many forms, including, but not limited to, non-volatile media, volatile media and transmission media. Non-volatile media include, for example, optical or magnetic disks, such as storage device 1408. Volatile media include, for example, dynamic memory 1404. Transmission media include, for example, coaxial cables, copper wire, fiber optic cables, and waves that travel through space without wires or cables, such as acoustic waves and electromagnetic waves, including radio, optical and infrared waves. Computer-readable storage medium refers to volatile or non-volatile media, but not transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read.

Network link 1478 typically provides information communication through one or more networks to other devices that use or process the information. For example, network link 1478 may provide a connection through local network 1480 to a host computer 1482 or to equipment 1484 operated by an Internet Service Provider (ISP). ISP equipment 1484 in turn provides data communication services through the public, world-wide packet-switching communication network of networks now commonly referred to as the Internet 1490. A computer called a server 1492 connected to the Internet provides a service in response to information received over the Internet. For example, server 1492 provides information representing video data for presentation at display 1414.

The invention is related to the use of computer system 1400 for implementing the techniques described herein. According to one embodiment of the invention, those techniques are performed by computer system 1400 in response to processor 1402 executing one or more sequences of one or more instructions contained in memory 1404. Such instructions, also called software and program code, may be read into memory 1404 from another computer-readable medium such as storage device 1408. Execution of the sequences of instructions contained in memory 1404 causes processor 1402 to perform the method steps described herein. In alternative embodiments, hardware, such as application specific integrated circuit 1420, may be used in place of or in combination with software to implement the invention. Thus, embodiments of the invention are not limited to any specific combination of hardware and software.

The signals transmitted over network link 1478 and other networks through communications interface 1470, carry information to and from computer system 1400. Computer system 1400 can send and receive information, including program code, through the networks 1480, 1490 among others, through network link 1478 and communications interface 1470. In an example using the Internet 1490, a server 1492 transmits program code for a particular application, requested by a message sent from computer 1400, through Internet 1490, ISP equipment 1484, local network 1480 and communications interface 1470. The received code may be executed by processor 1402 as it is received, or may be stored in storage device 1408 or other non-volatile storage for later execution, or both. In this manner, computer system 1400 may obtain application program code in the form of a signal on a carrier wave.

Various forms of computer readable media may be involved in carrying one or more sequence of instructions or data or both to processor 1402 for execution. For example, instructions and data may initially be carried on a magnetic disk of a remote computer such as host 1482. The remote computer loads the instructions and data into its dynamic memory and sends the instructions and data over a telephone line using a modem. A modem local to the computer system 1400 receives the instructions and data on a telephone line and uses an infra-red transmitter to convert the instructions and data to a signal on an infra-red a carrier wave serving as the network link 1478. An infrared detector serving as communications interface 1470 receives the instructions and data carried in the infrared signal and places information representing the instructions and data onto bus 1410. Bus 1410 carries the information to memory 1404 from which processor 1402 retrieves and executes the instructions using some of the data sent with the instructions. The instructions and data received in memory 1404 may optionally be stored on storage device 1408, either before or after execution by the processor 1402.

6. Extensions and Alternatives.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A method for modeling living biological systems, comprising:
determining a plurality of state variables y that indicate relevant properties of a living biological system;
determining a plurality of perturbation variables u that indicate factors that might affect one or more of the relevant properties of the biological system;
determining a measurable subset $\Omega$ of the plurality of state variables y, wherein a measureable variable of $\Omega$ is a state variable for which a value can be derived based on a measurement;
receiving measurement-based values Y for the measurable variables in $\Omega$;
determining model constants automatically on a processor based on the measured values Y, including determining a numerical value for a constant interaction factor $w_{ij}$ between a first state variable $y_i$ and a second state variable $y_j$ such that a change in a value of $y_i$ over time depends, at least in part, on a non-linear transformation of a sum of a value of a perturbation variable $u_i$ that affects $y_i$ added to a sum of all non-zero values for a product of $w_{ij}$ and $y_j$ for all state variables in the plurality of state variables;
determining model data that indicates the model constants, the plurality of state variables y and the plurality of perturbation variables u for a model that predicts a temporal change in $y_i$ based on values for the plurality of state variables y and for a perturbation variable $u_i$ and writing model data to a computer-readable medium.

2. The method as recited in claim 1, wherein determining the value for the constant interaction factor $w_{ij}$ further comprises determining a constant interaction factor $w_{ij}$ for every state variable $y_i$.

3. The method as recited in claim 1, wherein:
the non-linear transformation is proportional to a sigmoid function by a constant factor $\beta_i$; and
determining the model constants further comprises determining a value for the constant factor $\beta_i$.

4. The method as recited in claim 1, wherein:
a change in a value of $y_i$ over time depends, at least in part on a constant relaxation factor $\alpha_i$ that returns a deviation from a normal value for a state variable back toward the normal value; and
determining the model constants further comprises determining a value for the constant relaxation factor $\alpha_i$.

5. The method as recited in claim 1, further comprising using the model data to determine a pathway for processes in the living biological system based on the $w_{ij}$.

6. The method as recited in claim 1, further comprising using the model data to predict resulting values for the plurality of state variables y, based on initial values for the plurality of state variables and trial values for one or more of the plurality of perturbation variables u.

7. The method as recited in claim 6, further comprising conducting an experiment on a living biological system to measure values for the measurable subset Ω of the plurality of state variables y after perturbing the living biological system as determined by the trial values for the plurality of perturbation variables.

8. The method as recited in claim 7, wherein:
receiving the measurement-based values Y for the measurable variables in Ω further comprises receiving the measurement-based values Y from each of a plurality of experiments;
each experiment of the plurality of experiments comprises non-zero values for at least two of the plurality of perturbation variables; and
each perturbation variable of the plurality of perturbation variables has a non-zero value in at least one of the plurality of experiments.

9. The method as recited in claim 1, further comprising using the model data to determine a particular set of values for the plurality of perturbation variables, wherein the particular set of values causes initial values for the plurality of state variables to change with time to desired values for one or more of the plurality of state variables.

10. The method as recited in claim 1, wherein a particular state variable of the plurality of state variables holds data that indicates cell phenotype.

11. The method as recited in claim 1, wherein a particular state variable of the plurality of state variables holds data that indicates apoptosis.

12. The method as recited in claim 1, wherein a particular state variable of the plurality of state variables holds data that indicates an amount of a particular protein.

13. The method as recited in claim 1, wherein a particular state variable of the plurality of state variables holds data that indicates a relative population of a particular molecular fragment measureable in a mass spectrometer.

14. The method as recited in claim 13, wherein:
receiving the measurement-based values Y for the measurable variables in Ω further comprises receiving the measurement-based values Y from each of a plurality of experiments;
each experiment of the plurality of experiments comprises non-zero values for at least two of the plurality of perturbation variables; and
each perturbation variable of the plurality of perturbation variables has a non-zero value in at least one of the plurality of experiments.

15. The method as recited in claim 1, wherein a particular perturbation variable of the plurality of perturbation variables holds data that indicates an amount of a particular substance, such as an element, a chemical compound, an antibody and a nucleic acid.

16. The method as recited in claim 1, wherein a particular perturbation variable of the plurality of perturbation variables holds data that indicates a genetic alteration of the gene content of the living biological system.

17. The method as recited in claim 1, wherein a particular perturbation variable of the plurality of perturbation variables holds data that indicates an amount of a particular physical environment, such as temperature, pressure, electrical charge, electromagnetic radiation, and pH.

18. The method as recited in claim 17, wherein:
receiving the measurement-based values Y for the measurable variables in Ω further comprises receiving the measurement-based values Y from each of a plurality of experiments;
each experiment of the plurality of experiments comprises non-zero values for at least two of the plurality of perturbation variables; and
each perturbation variable of the plurality of perturbation variables has a non-zero value in at least one of the plurality of experiments.

19. The method as recited in claim 1, wherein a particular plurality of perturbation variables of the plurality of perturbation variables holds data that indicates an arithmetic factor of therapeutic doses of a corresponding number of drugs, whereby a model based on the model data predicts combinatorial effects of drug therapies.

20. The method as recited in claim 1, wherein the living biological system is a cancer cell and a particular state variable of the plurality of state variables holds data that indicates a G1 phase arrest.

21. The method as recited in claim 1, wherein determining the value for the interaction factor $w_{ij}$ further comprises minimizing an error function that grows with a number of non-zero interaction factors $w_{ij}$.

22. The method as recited in claim 21, wherein the error function decreases for each non-zero interaction factor $w_{ij}$ that is desired to conform to an accepted pathway.

23. The method as recited in claim 1, wherein determining model constants further comprises minimizing an error function that grows with a sum of squared differences between the measured values Y for the measurable variables in Ω and computed values for the corresponding measurable variables.

24. The method as recited in claim 1, wherein determining the value for the interaction factor $w_{ij}$ further comprises minimizing an error function for each of a plurality of structures for the model, wherein each structure adds a limited increment of non-zero interaction factors $w_{ij}$ to a set of seed structures, wherein each structure in the seed set has a limited number of non-zero interaction factors $w_{ij}$.

25. The method as recited in claim 24, wherein determining the value for the interaction factor $w_{ij}$ further comprises randomly selecting a subset of the plurality of structures based on a probability for each structure inversely related to its minimum error.

26. The method as recited in claim 25, wherein:
receiving the measurement-based values Y for the measurable variables in Ω further comprises receiving the measurement-based values Y from each of a plurality of experiments;
each experiment of the plurality of experiments comprises non-zero values for at least two of the plurality of perturbation variables; and
each perturbation variable of the plurality of perturbation variables has a non-zero value in at least one of the plurality of experiments.

27. A method for outputting values for a plurality of state variables, wherein each of said method steps is performed on a processor, comprising:
receiving a set of initial state values for a plurality of state variables y that indicate relevant properties of a living biological system;
receiving model data that includes values for a plurality of automatically determined, numerical, constant interaction factors $w_{ij}$ between pairs of state variables;
receiving a set of trial values for a plurality of perturbation variables u that indicate factors that might affect one or more of the relevant properties of the biological system; and
determining a change over time in a value for a particular state variable $y_i$, of the plurality of state variables based, at least in part, on a non-linear transformation of a sum of the trial value for the perturbation variable $u_i$ that affects $y_i$ added to a sum of all non-zero values for a product of $w_{ij}$ and $y_j$ over all state variables in the plurality of state variables.

28. A non-transitory computer-readable medium carrying one or more sequences of instructions for modeling a living biological system, wherein execution of the one or more sequences of instructions by one or more processors causes an apparatus to perform the steps of:
receiving state data that indicates a plurality of state variables y that indicate relevant properties of a living biological system;
receiving perturbation data that indicates a plurality of perturbation variables u that indicate factors that might affect one or more of the relevant properties of the biological system;
receiving measurable data that indicates a measurable subset Ω of the plurality of state variables y, wherein a measureable variable of Ω is a state variable for which a value can be derived based on a measurement;
receiving measurement-based values Y for the measurable variables in Ω;
determining model constants automatically based on the measured values Y, including determining a numerical value for a constant interaction factor $w_{ij}$ between a first state variable $y_i$ and a second state variable $y_j$ such that a change in a value of $y_i$ over time depends, at least in part, on a non-linear transformation of a sum of a value of a perturbation variable $u_i$ that affects $y_i$ added to a sum of all non-zero values for a product of $w_{ij}$ and $y_j$ for all state variables in the plurality of state variables;
determining model data that indicates the model constants, the plurality of state variables y and the plurality of perturbation variables u for a model that predicts a temporal change in $y_i$ based on values for the plurality of state variables y and for a perturbation variable $u_i$, and
writing the model data to a computer-readable medium.

29. A non-transitory computer-readable medium carrying one or more sequences of instructions for modeling a living biological system, wherein execution of the one or more sequences of instructions by one or more processors causes the one or more processors to perform the steps of:
receiving a set of initial state values for a plurality of state variables y that indicate relevant properties of a living biological system;
receiving model data that includes values for a plurality of automatically determined, numerical, constant interaction factors $w_{ij}$ between pairs of state variables;
receiving a set of trial values for a plurality of perturbation variables u that indicate factors that might affect one or more of the relevant properties of the biological system; and
determining a change over time in a value for a particular state variable $y_i$ of the plurality of state variables based, at least in part, on a non-linear transformation of a sum of the trial value for the perturbation variable $u_i$ that affects $y_i$ added to a sum of all non-zero values for a product of $w_{ij}$ and $y_j$ over all state variables in the plurality of state variables.

30. A method for screening drugs for treating a biological system, wherein each of said method steps is performed on a processor, comprising:
receiving a set of initial state values for a plurality of state variables y that indicate relevant properties of a living biological system;
receiving model data that includes values for a plurality of automatically determined, numerical, constant interaction factors $w_{ij}$ between pairs of state variables;
receiving a set of trial values for a set of one or more drugs that might affect one or more of the relevant properties of the biological system;
determining a change over time in a value for a particular state variable $y_i$ of the plurality of state variables based, at least in part, on a non-linear transformation of a sum of the set of trial values that affect $y_i$ added to a sum of all non-zero values for a product of $w_{ij}$ and $y_j$ over all state variables in the plurality of state variables; and
determining efficacy of the set of trial values for the set of one or more drugs in treating the biological system based on the change over time in the particular state variable.

31. The method as recited in claim 26, further comprising determining whether the efficacy of the set of trial values for the set of one or more drugs exceeds a threshold value; and
if it is determined that the efficacy exceeds the threshold value, then selecting the set of one or more drugs for therapeutic use.

32. A system for modeling living biological systems, comprising:
one or more computer-readable media configured to store data indicating:
a plurality of state variables y that indicate relevant properties of a living biological system;
a plurality of perturbation variables u that indicate factors that might affect one or more of the relevant properties of the biological system;
a measurable subset Ω of the plurality of state variables y, wherein a measureable variable of Ω is a state variable for which a value can be derived based on a measurement; and
a set of one or more processors configured to perform the following:
receive measurement-based values Y for the measurable variables in Ω;
determine model constants automatically on a processor based on the measured values Y, including determining a numerical value for a constant interaction factor $w_{ij}$ between a first state variable $y_i$ and a second state variable $y_j$ such that a change in a value of $y_i$ over time depends, at least in part, on a non-linear transformation of a sum of a value of a perturbation variable $u_i$ that affects $y_i$ added to a sum of all non-zero values for a product of $w_{ij}$ and $y_j$ for all state variables in the plurality of state variables;
determine model data that indicates the model constants, the plurality of state variables y and the plurality of perturbation variables u for a model that predicts a temporal change in $y_i$ based on values for the plurality of state variables y and for a perturbation variable $u_1$ and
write model data to a computer-readable medium.

33. A system for outputting values for a plurality of state variables comprising a set of one or more processors configured to perform the following:
receiving a set of initial state values for a plurality of state variables y that indicate relevant properties of a living biological system;
receiving model data that includes values for a plurality of automatically determined, numerical, constant interaction factors $w_{ij}$ between pairs of state variables;
receiving a set of trial values for a plurality of perturbation variables u that indicate factors that might affect one or more of the relevant properties of the biological system; and determining a change over time in a value for a particular state variable $y_i$ of the plurality of state variables based, at least in part, on a non-linear transformation of a sum of the trial value for the perturbation variable $u_i$ that affects $y_i$ added to a sum of all non-zero values for a product of $w_{ij}$ and $y_j$ over all state variables in the plurality of state variables.

34. A system for screening drugs for treating a biological system comprising a set of one or more processors configured to perform the following:

receiving a set of initial state values for a plurality of state variables y that indicate relevant properties of a living biological system;

receiving model data that includes values for a plurality of automatically determined, numerical, constant interaction factors $w_{ij}$ between pairs of state variables;

receiving a set of trial values for a set of one or more drugs that might affect one or more of the relevant properties of the biological system;

determining a change over time in a value for a particular state variable $y_i$ of the plurality of state variables based, at least in part, on a non-linear transformation of a sum of the set of trial values that affect $y_i$ added to a sum of all non-zero values for a product of $w_{ij}$ and $y_j$ over all state variables in the plurality of state variables; and determining efficacy of the set of trial values for the set of one or more drugs in treating the biological system based on the change over time in the particular state variable.

* * * * *